(12) United States Patent
Christian et al.

(10) Patent No.: US 9,788,891 B2
(45) Date of Patent: Oct. 17, 2017

(54) ABLATION ELECTRODE ASSEMBLIES AND METHODS FOR USING SAME

(75) Inventors: Steven C. Christian, New Brighton, MN (US); Reed R. Heimbecher, Hamel, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1151 days.

(21) Appl. No.: 12/979,803

(22) Filed: Dec. 28, 2010

(65) Prior Publication Data

US 2012/0165809 A1 Jun. 28, 2012

(51) Int. Cl.
*A61B 18/14* (2006.01)
*A61B 18/00* (2006.01)

(52) U.S. Cl.
CPC *A61B 18/1492* (2013.01); *A61B 2018/00101* (2013.01); *A61B 2018/00714* (2013.01); *A61B 2018/00791* (2013.01); *A61B 2218/002* (2013.01)

(58) Field of Classification Search
CPC A61B 2018/00011; A61B 2018/00029; A61B 2018/142; A61B 2018/00005; A61B 2018/00023
USPC ................................... 606/45–46; 80/45–46
See application file for complete search history.

(56) References Cited

U.S. PATENT DOCUMENTS

| 5,290,263 A | 3/1994 | Wigness et al. |
|---|---|---|
| 5,348,554 A | 9/1994 | Imran et al. |
| 5,688,267 A | 11/1997 | Panescu et al. |
| 5,735,846 A | 4/1998 | Panescu et al. |
| 5,792,140 A | 8/1998 | Tu et al. |
| 5,897,552 A | 4/1999 | Edwards et al. |
| 5,902,328 A * | 5/1999 | LaFontaine ........ A61B 18/1485 600/373 |

(Continued)

FOREIGN PATENT DOCUMENTS

| EP | 2204132 A1 | 7/2010 |
|---|---|---|
| JP | 2010-505596 A | 2/2010 |

(Continued)

OTHER PUBLICATIONS

"International Search Report and Written Opinion", PCT/US2011/059111 dated Apr. 13, 2012.

(Continued)

*Primary Examiner* — Jaymi Della
(74) *Attorney, Agent, or Firm* — Dykema Gossett PLLC

(57) ABSTRACT

Ablation electrode assemblies include an inner core member and an outer shell surrounding the inner core member. The inner core member and the outer shell define a space or separation region therebetween. The inner core member is constructed from a thermally insulative material having a reduced thermal conductivity. In an embodiment, the space is a sealed or evacuated region. In other embodiments, irrigation fluid flows within the space. The ablation electrode assembly further includes at least one thermal sensor in some embodiments. Methods for providing irrigation fluid during cardiac ablation of targeted tissue are disclosed that include calculating the energy delivered to irrigation fluid as it flows within the ablation electrode assembly through temperature measurement of the irrigation fluid. Pulsatile flow of irrigation fluid can be utilized in some embodiments of the disclosure.

7 Claims, 12 Drawing Sheets

(56) References Cited

U.S. PATENT DOCUMENTS

| | | | |
|---|---|---|---|
| 6,010,500 A | 1/2000 | Sherman et al. | |
| 6,017,338 A | 1/2000 | Brucker et al. | |
| 6,068,653 A | 5/2000 | LaFontaine | |
| 6,233,476 B1 | 5/2001 | Strommer et al. | |
| 6,328,735 B1 | 12/2001 | Curley et al. | |
| 6,464,700 B1* | 10/2002 | Koblish | A61B 18/1482 600/374 |
| 6,498,944 B1 | 12/2002 | Ben-Haim et al. | |
| 6,506,189 B1 | 1/2003 | Rittman et al. | |
| 6,522,930 B1 | 2/2003 | Schaer et al. | |
| 6,575,969 B1 | 6/2003 | Rittman et al. | |
| 6,579,288 B1* | 6/2003 | Swanson et al. | 606/41 |
| 6,616,655 B1 | 9/2003 | Falwell et al. | |
| 6,690,963 B2 | 2/2004 | Ben-Haim et al. | |
| 6,788,967 B2 | 9/2004 | Ben-Haim et al. | |
| 6,936,047 B2 | 8/2005 | Nasab et al. | |
| 7,197,354 B2 | 3/2007 | Sobe | |
| 7,263,397 B2 | 8/2007 | Hauck et al. | |
| RE39,863 E | 10/2007 | Smith | |
| 7,344,533 B2 | 3/2008 | Pearson et al. | |
| 7,386,339 B2 | 6/2008 | Strommer et al. | |
| 7,389,148 B1 | 6/2008 | Morgan | |
| 7,536,218 B2 | 5/2009 | Govari et al. | |
| 7,591,816 B2 | 9/2009 | Wang et al. | |
| 7,776,034 B2 | 8/2010 | Kampa | |
| 7,815,635 B2 | 10/2010 | Wittkampf et al. | |
| 7,824,406 B2 | 11/2010 | Wang et al. | |
| 7,826,905 B2 | 11/2010 | Chitre et al. | |
| 2002/0123749 A1 | 9/2002 | Jain | |
| 2003/0004506 A1 | 1/2003 | Messing | |
| 2003/0060822 A1 | 3/2003 | Schaer et al. | |
| 2003/0195510 A1 | 10/2003 | Schaer | |
| 2004/0215183 A1 | 10/2004 | Hoey et al. | |
| 2005/0055019 A1* | 3/2005 | Skarda | 606/41 |
| 2005/0090816 A1 | 4/2005 | McClurken et al. | |
| 2006/0287650 A1 | 12/2006 | Cao et al. | |
| 2007/0043349 A1* | 2/2007 | Swanson et al. | 606/41 |
| 2007/0049915 A1 | 3/2007 | Haemmerich et al. | |
| 2007/0270791 A1 | 11/2007 | Wang et al. | |
| 2008/0065062 A1 | 3/2008 | Leung et al. | |
| 2008/0071267 A1 | 3/2008 | Wang et al. | |
| 2008/0091193 A1 | 4/2008 | Kauphusman et al. | |
| 2008/0147060 A1* | 6/2008 | Choi | A61B 18/1477 606/42 |
| 2008/0161795 A1 | 7/2008 | Wang et al. | |
| 2008/0167646 A1 | 7/2008 | Godara et al. | |
| 2008/0294158 A1 | 11/2008 | Pappone et al. | |
| 2009/0093811 A1 | 4/2009 | Koblish et al. | |
| 2009/0125016 A1 | 5/2009 | Wang et al. | |
| 2009/0125017 A1 | 5/2009 | Wang et al. | |
| 2009/0163911 A1 | 6/2009 | Cao et al. | |
| 2009/0163913 A1 | 6/2009 | Wang et al. | |
| 2009/0171187 A1 | 7/2009 | Gerhart et al. | |
| 2009/0171188 A1 | 7/2009 | Paul et al. | |
| 2009/0177193 A1 | 7/2009 | Wang et al. | |
| 2009/0240248 A1 | 9/2009 | Deford et al. | |
| 2009/0240249 A1 | 9/2009 | Chan et al. | |
| 2009/0312756 A1* | 12/2009 | Schlesinger et al. | 606/41 |
| 2010/0057072 A1 | 3/2010 | Roman et al. | |
| 2010/0069921 A1 | 3/2010 | Miller et al. | |
| 2010/0137859 A1 | 6/2010 | Wang | |
| 2010/0152727 A1 | 6/2010 | Gibson | |
| 2010/0152731 A1 | 6/2010 | de la Rama et al. | |
| 2010/0168729 A1 | 7/2010 | Wang et al. | |
| 2010/0168736 A1 | 7/2010 | Wang | |
| 2010/0174177 A1 | 7/2010 | Wu | |
| 2010/0286684 A1 | 11/2010 | Hata et al. | |
| 2011/0092969 A1 | 4/2011 | Wang et al. | |
| 2011/0118724 A1* | 5/2011 | Turner | A61B 18/1815 606/33 |
| 2011/0264089 A1* | 10/2011 | Zirkle et al. | 606/41 |
| 2011/0282342 A1* | 11/2011 | Leo | A61B 18/1492 606/33 |
| 2012/0035605 A1* | 2/2012 | Tegg et al. | 606/41 |

FOREIGN PATENT DOCUMENTS

| | | |
|---|---|---|
| WO | 03/024349 A1 | 3/2003 |
| WO | 2008/045925 A2 | 4/2008 |
| WO | 2008082988 | 10/2008 |
| WO | 2008083000 | 10/2008 |
| WO | 2008083003 | 10/2008 |
| WO | 2009082574 | 2/2009 |
| WO | 2009070446 | 4/2009 |
| WO | 2012/091793 A1 | 7/2012 |

OTHER PUBLICATIONS

International Search Report and Written Opinion of ISA for PCT/US2012/023355 dated Jun. 4, 2012.

International Search Report and Written Opinion of ISA for PCT/US2012/026759 dated Jul. 5, 2012.

* cited by examiner

ABLATION ELECTRODE ASSEMBLIES AND METHODS FOR USING SAME

BACKGROUND OF THE INVENTION a. Field of the Invention

The instant disclosure relates generally to ablation electrode assemblies. In particular, the instant disclosure relates to ablation electrode assemblies having an inner core member and an outer shell surrounding the inner core member, wherein the inner core member and the outer shell define a space therebetween. In some embodiments, the space can comprise a vacuum region or evacuated region, and in other embodiments the space can be configured for allowing the flow of irrigation fluid. The instant disclosure further relates to methods of using ablation electrode assemblies, including methods for providing irrigation fluid during cardiac ablation of targeted tissue in a human body.

b. Background Art

Electrophysiology catheters are used in a variety of diagnostic and/or therapeutic medical procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions and stasis of blood flow in a chamber of a heart which can lead to a variety of symptomatic and asymptomatic ailments and even death.

A medical procedure in which an electrophysiology catheter is used includes a first diagnostic catheter deployed through a patient's vasculature to a patient's heart or a chamber or vein thereof. An electrophysiology catheter that carries one or more electrodes can be used for cardiac mapping or diagnosis, ablation and/or other therapy delivery modes, or both. Once at the intended site, treatment can include, for example, radio frequency (RF) ablation, cryoablation, laser ablation, chemical ablation, high-intensity focused ultrasound-based ablation, microwave ablation. An electrophysiology catheter imparts ablative energy to cardiac tissue to create one or more lesions in the cardiac tissue and oftentimes a contiguous or linear and transmural lesion. This lesion disrupts undesirable cardiac activation pathways and thereby limits, corrals, or prevents errant conduction signals that can form the basis for arrhythmias.

During RF ablation, local temperature elevation can result in coagulum formation on the ablation electrode, resulting in an impedance rise. As the impedance increases, more energy is passed through the portion of the electrode without coagulation, creating even higher local temperatures and further increasing coagulum formation and the impedance. Finally, enough blood coagulates onto the electrode that no energy passes into the targeted tissue, thereby requiring the catheter to be removed from the vascular system, the electrode to be cleaned, and the catheter to be repositioned within the cardiac system at the desired location. Not only can this process be time consuming, but it can be difficult to return to the previous location because of the reduced electrical activity in the targeted tissue, which has been previously ablated. Recent studies have also demonstrated the formation of a so-called soft thrombus in RF ablation. The formation of the soft thrombus results from heat induced protein denaturation and aggregation and occurs independently of heparin concentration in serum. In addition, RF ablation can generate significant heat, which, if not controlled, can result in excessive tissue damage, such as tissue charring, steam pop, and the like.

Accordingly, it can be desirable to monitor and/or control the temperature of ablation electrode assemblies. It can also be desirable to use ablation electrode assemblies to provide irrigation fluid during RF ablation. RF ablation catheters can be configured to provide temperature feedback during RF ablation via a thermal sensor such as a thermocouple or thermistor. A temperature reading provided by a single thermal sensor cannot accurately represent the temperature of the electrode/tissue interface. This is because a portion of the electrode that is in direct contact with the targeted tissue can have a higher temperature than the rest of the electrode that is being cooled by the blood flow. The orientation of the RF ablation catheter can affect the position of the thermal sensor, and accordingly, can affect the temperature reading provided by the thermal sensor. If the thermal sensor is in contact with the targeted tissue, the thermal sensor can provide a certain temperature reading generally corresponding to the temperature of the targeted tissue, but if the thermal sensor is not in contact with the targeted tissue, there will be a time lag before the thermal sensor provides a temperature reading generally corresponding to the temperature of the targeted tissue, and due to the cooling effect of the blood flow, the thermal sensor can never approach the actual temperature of the targeted tissue. In an effort to overcome the effect that the orientation of the catheter can have on temperature sensing, multiple thermal sensors positioned at different locations on the electrode can be used. For example and without limitation, the highest measured temperature can be used to represent the electrode/tissue interface temperature. However, temperature measurements provided by multiple thermal sensors cannot always accurately reflect the temperature of the electrode/tissue interface (e.g., heat transfer between the multiple thermal sensors can affect the temperature reading of each thermal sensor).

BRIEF SUMMARY OF THE INVENTION

It is desirable to be able to provide ablation electrode assemblies that are configured to mitigate the effects of orientation of the RF ablation catheter for monitoring the temperature of the ablation electrode assemblies and/or targeted tissue, as well as to mitigate temperature gradients (i.e., the directions and rates at which temperature changes) across electrodes. It is also desirable to interrupt and/or reduce heat transfer paths between multiple thermal sensors of the electrode, thereby improving the ability to distinguish between the temperature reading associated with a thermal sensor that is proximate the lesion formed in the targeted tissue and the temperature reading associated with a thermal sensor that is proximate the circulating blood pool. It is also desirable to have improved temperature correlation between the electrode and tissue interface.

It is also desirable, in some embodiments, to segment the ablation electrode and have an independent thermal sensor associated with each segment of the ablation electrode in order to offer even more complete segregation of the individual thermal sensors.

It is also desirable, in some embodiments, to include a mechanism to irrigate the ablation electrode assemblies and/or targeted areas in a patient's body with biocompatible fluids, such as saline solution, in order to reduce charring and inhibit the formation of coagulum and/or soft thrombus, as well as to enable deeper and/or greater volume lesions as compared to conventional, non-irrigated catheters at identical power settings. This can, in turn, enable greater energy delivery during RF ablation. The flow of biocompatible fluids (i.e., irrigation fluids) can be turbulent in order to provide an enveloping flow pattern adjacent to the surface of the ablation electrode assemblies for mixing with, displacing, and/or diluting blood that can be in contact with the ablation electrode assemblies in order to prevent stasis and the formation of coagulum. Pulsatile flow of irrigation fluids can help prevent stagnation areas at the distal end of an electrode by increasing flow turbulence around the catheter. Pulsatile flow of irrigation fluids can also improve correlation between the temperature of the electrode tip and the targeted tissue. The flow of irrigation fluids can be modified based on information and feedback received during RF ablation.

It is also desirable, in some embodiments, to monitor a change in the temperature of irrigation fluids during RF ablation in order to provide additional information or feedback regarding energy delivery and/or the temperature of the electrode and tissue interface. RF ablation can be modified based on the information and feedback regarding energy delivery and/or the temperature of the electrode and tissue interface. Operation in a temperature control mode can be at a set point above 55 degrees Celsius.

The instant disclosure relates to an ablation electrode assembly including an inner core member having a distal end and proximal end and an outer shell surrounding the inner core member. The outer shell also has a distal end and a proximal end. The inner core member and outer shell define a space (as used herein the term "space" includes, for example, a volume or cavity or region). Herein, the term "annular" is used to describe the space; however, the configuration of the space can vary greatly and can be regular or irregular and can include support members (e.g., flutes, bosses, posts, and the like) to maintain separation and a useable space between the core and the shell. The spacing between the core and the shell can vary, if desired, and the distal end of the ablation electrode can be hemispherical, circular (e.g., the core and shell comprise a pair of concentric cylinders), rounded, geometrically-shaped, or the like. In an embodiment, the annular space can comprise a vacuum region or evacuated region. The inner core member and outer shell can both be generally cylindrical in shape with a distal end that is generally hemispherical in shape. The inner core member can comprise a thermal insulator having a reduced thermal conductivity, whereas the outer shell can comprise an electrically conductive material. The inner core member can include at least one channel configured to receive a thermal sensor, and the ablation electrode assembly can include at least one thermal sensor disposed in the channel. The inner core member can include an outer surface, an inner surface defining an inner cavity, and a radially extending passageway that extends from the inner cavity to the outer surface of the inner core member. As used herein, the term "radially extending" means extending away from the longitudinal axis at any angle relative to the longitudinal axis of the ablation electrode assembly. The inner core member can further include an axially extending passageway extending from an inner cavity of the inner core member to the distal end of the inner core member. In an embodiment, the outer shell can be scored with a plurality of axially extending grooves or slots to separate the outer shell into a plurality of segments. Each of the plurality of segments of the outer shell can have a corresponding thermal sensor.

The ablation electrode assembly can further include an irrigant distribution element. The irrigation distribution element can be configured as a generally annular ring in accordance with an embodiment of the disclosure. The irrigation distribution element has a proximal end and a distal end. The distal end of the irrigant distribution element can define a circumferential irrigation port between the irrigant distribution element and the inner core member.

In an embodiment of the disclosure, irrigation fluid can flow within at least a portion of at least one of the inner core member and outer shell. Irrigation fluid can flow from the inner cavity through the radially extending passageways in an embodiment with only proximal delivery of irrigation fluid. Irrigation fluid can flow from the inner cavity through the axially extending passageway in an embodiment with distal delivery of irrigation fluid. Irrigation fluid can also flow through the space between the inner core member and outer shell. In an embodiment of the disclosure, irrigation fluid has a first flow rate in a first time period and a second flow rate in a second time period. The first flow rate and the second flow rate can alternate and recur at intervals over time in accordance with an embodiment of the disclosure. In some embodiments, the second flow rate is greater than the first flow rate. For example and without limitation, the first flow rate can be approximately less than or about two (2) milliliters per minute (ml/min.), and the second flow rate can be approximately 13 ml/min. In other embodiments, the first flow rate is greater than the second flow rate and in yet other embodiments a single very low flow rate can be implemented (at least vis-à-vis the prior known or typical irrigation fluid flow rates), for example, on the order of between about one ml/min. and less than about 13 ml/min. In some embodiments the first and second flow rates can be determined based on at least in part on a temperature measurement taken by a thermal sensor disposed on the inner core member. In some embodiments, the first and second flow rates can be determined based at least in part on an impedance measurement taken by a positioning electrode located on a catheter incorporating the ablation electrode assembly. Accordingly, the first and second flow rates for irrigation fluid are based on feedback provided by the ablation electrode assembly, including feedback regarding temperature and/or impedance, for example and without limitation.

In an embodiment of the disclosure, a method for providing irrigation fluid during cardiac ablation of targeted tissue includes the step of using a catheter having a catheter shaft having a fluid lumen; and an electrode assembly connected to the catheter shaft. The electrode assembly includes an inner core member having a distal end and a proximal end and an outer shell having a distal end and a proximal end. The inner core member further includes an outer surface, an inner surface defining a cavity, and an axially extending passageway extending from the cavity to the distal end of the inner core member. The outer shell surrounds the inner core member, such that the inner core member and the outer shell define a space. The method further includes the following steps: delivering energy to the outer shell of the electrode assembly; directing irrigation fluid from the fluid lumen to the cavity of the inner core member; allowing at least a first portion of the irrigation fluid from the cavity of the inner core member to flow in the space between the inner core member and the outer shell; directing at least the first portion of the irrigation fluid away from the space between the inner core member and the outer shell; measuring a first temperature of at least the first portion of the irrigation fluid near a first location where at least the first portion of the irrigation fluid enters the cavity of the inner core member; measuring a second temperature of at least the first portion of the irrigation fluid near a second location where at least the first portion of the irrigation fluid exits the electrode assembly; calculating a temperature differential value based at least in part on the first temperature and the second temperature; calculating a first value indicative of energy delivered to at least the first portion of the irrigation fluid as it flows from the first location to the second location based at least in part on the temperature differential value; and calculating a second value indicative of energy delivered to the targeted tissue based at least in part on the first value indicative of energy delivered to at least the first portion of the irrigation fluid. In an embodiment of the disclosure, the inner core member includes a first radially extending passageway that extends through the outer surface of the inner core member. At least the first portion of the irrigation fluid can be directed away from the space between the inner core member and the outer shell to the first radially extending passageway in an embodiment. In other embodiments, at least the first portion of the irrigation fluid is directed away from the space between the inner core member and the outer shell toward a proximal end of the catheter for elimination from the catheter at a location that is remote from a patient. In an embodiment of the disclosure, the inner core member includes a second radially extending passageway that extends from the inner cavity to the outer surface of the inner core member.

The method for providing irrigation fluid during cardiac ablation of targeted tissue further includes the steps of directing at least a second portion of the irrigation fluid from the inner cavity of the inner core member directly to the second radially extending passageway. The first portion of the irrigation fluid can be separate from the second portion of the irrigation fluid. A flow rate of the first portion of the irrigation fluid can be independent of a flow rate of the second portion of the irrigation fluid. A flow rate of the second portion of the irrigation fluid can be greater than a flow rate of the first portion of the irrigation fluid with overall total fluid volumes much lower than prior art or typically utilized in clinical practice, especially valuable for patients already suffering from fluid overload (e.g., patient having heart failure and the like). That is, overall total fluid volume can range from low single digits to about ten or so milliliters per minute while effectively reducing or eliminating char and coagulum and improving temperature correlation for precise control of power to maintain a temperature during ablation procedures.

The outer shell of the electrode assembly can be electrically connected to an ablation system including an ablation generator for generating and delivering energy to the catheter. The energy generated and delivered to the catheter from the ablation generator is based at least in part on the highest temperature measurement from the plurality of thermal sensors in an embodiment of the disclosure. The energy generated and delivered to the catheter from the ablation generator can be based at least in part on the temperature differential value. The method for providing irrigation fluid during cardiac ablation of targeted tissue can further include the steps of correlating the temperature differential value to a temperature of the targeted tissue and determining the temperature of the targeted tissue based at least in part on the temperature differential value.

In an embodiment, another method for providing irrigation fluid during cardiac ablation of targeted tissue can include the step of using a catheter comprising a catheter shaft having a fluid lumen; and an electrode assembly connected to the catheter shaft. The electrode assembly can comprise an inner core member having a distal end and a proximal end; and an outer shell surrounding the inner core member. The inner core member and the outer shell can define a space. The method can further include the step of directing a pulsatile flow of irrigation fluid within at least a portion of at least one of the inner core member and outer shell. The irrigation fluid can have a first flow rate in a first time period and a second flow rate in a second time period. The first flow rate and the second flow rate can alternate and recur at intervals over time. In some embodiments, the second flow rate is greater than the first flow rate. For example and without limitation, the first flow rate can be approximately 2 ml/minute, and the second flow rate can be approximately 13 ml/minute. In other embodiments, the first flow rate is greater than the second flow rate and, as noted above, total flow rate (or volume delivered per unit of time) can be exceedingly low as compared to traditional irrigant flow rates (and volumes). In some embodiments, the first and second flow rates for irrigation fluid can be based on feedback provided by the ablation electrode assembly, including feedback regarding temperature and/or impedance, for example and without limitation.

In an embodiment of the disclosure, a system for providing irrigation fluid during cardiac ablation of targeted tissue includes a catheter comprising a catheter shaft having a fluid lumen and an electrode assembly connected to the catheter shaft. The system further includes a plurality of thermal sensors disposed within the catheter; an ablation generator electrically connected to at least a portion of the electrode assembly; an electronic control unit (ECU) operatively connected to each of the plurality of thermal sensors; and a control system. The ECU is configured to: receive as an input data from the plurality of thermal sensors relating to temperature measurements of irrigation fluid, determine a temperature differential value responsive to the data, determine a first value indicative of energy delivered to at a least a first portion of irrigation fluid, the first value responsive to the data, determine a second value indicative of energy delivered to the targeted tissue, the second value responsive to the data, and output the temperature differential value, the first value, and the second value. The control system is configured to receive the temperature differential value, the first value, and the second value and configured to control energy delivery of the ablation generator based at least in part on at least one of the temperature differential value, the first value, and the second value. The system can further include a sensor for measuring flow rates of irrigation fluid, and the ECU can be further configured to receive as an input data from the sensor relating to flow rates of irrigation fluid. The first value and the second value can be responsive to the data from the sensor relating to flow rates of irrigation fluid.

The ECU can be configured to correlate the temperature differential value to a temperature of the targeted tissue and store data relating to the correlation between the temperature differential value and the temperature of the targeted tissue. The control system can be configured to retrieve data relating to the correlation between the temperature differential value and the temperature of the targeted tissue and control energy delivery to the ablation generator based at least in part on the temperature differential value.

DETAILED DESCRIPTION OF THE DISCLOSURE

The instant disclosure generally relates to irrigated ablation electrode assemblies. For purposes of this description, similar aspects among the various embodiments described herein will be referred to by similar reference numbers. As will be appreciated, however, the structure of the various aspects can be different among the various embodiments.

Figure 1:
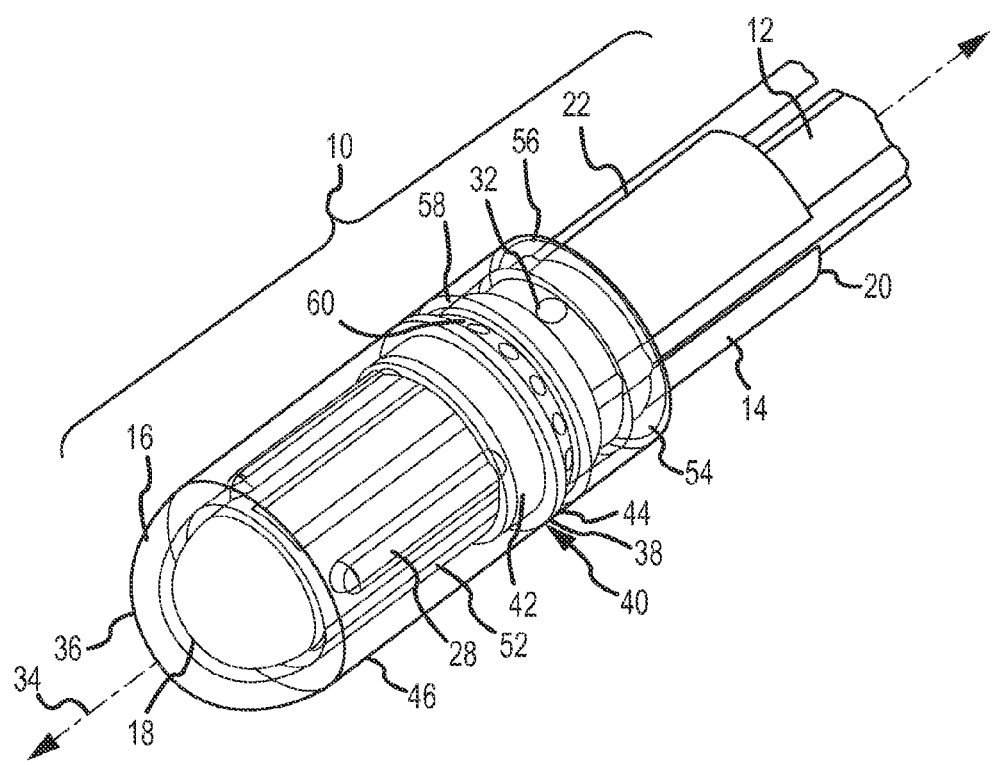
FIG. 1 is an isometric partially transparent view of an ablation electrode assembly in accordance with a first embodiment of the disclosure.
Figure 2:
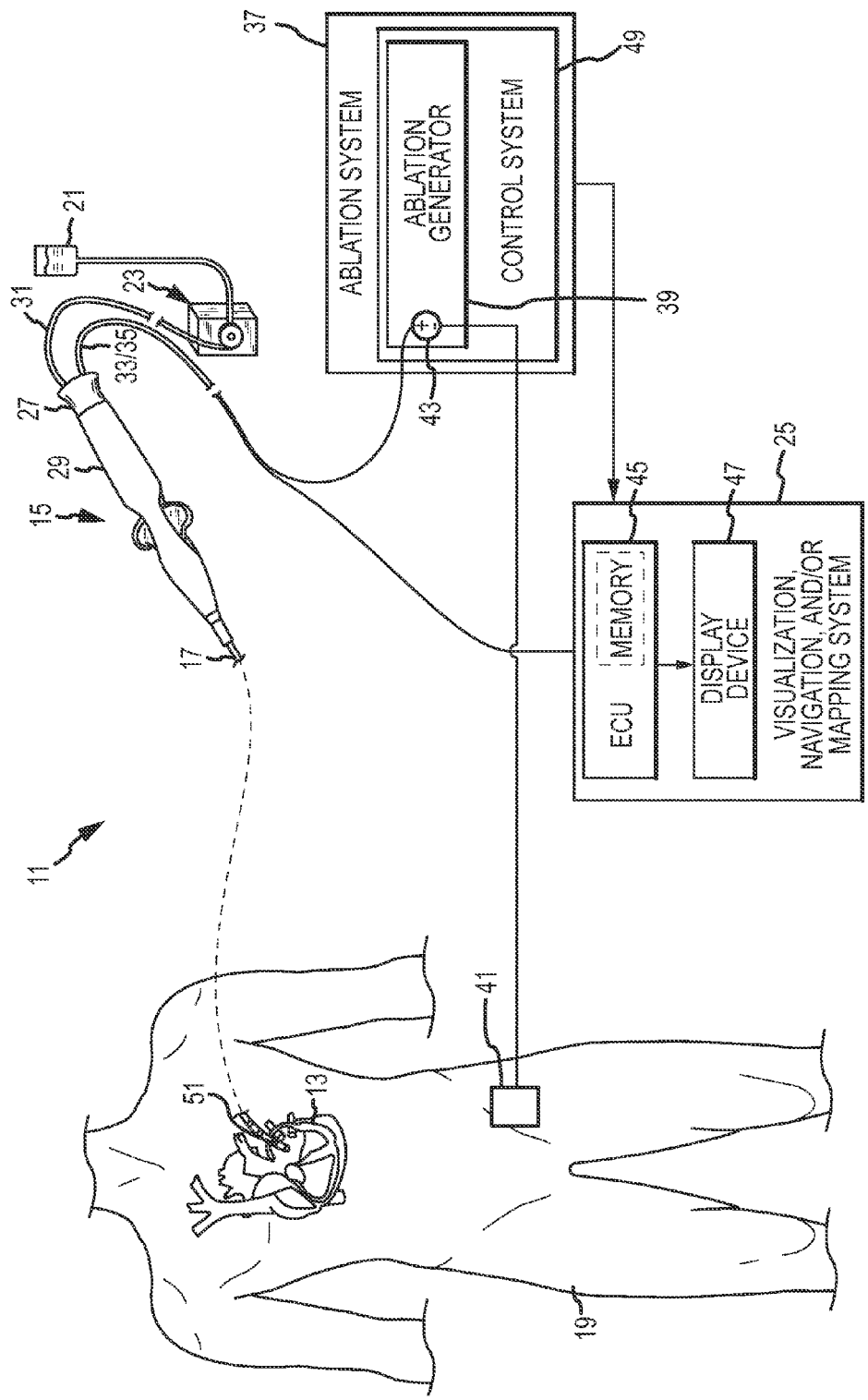
FIG. 2 is a diagrammatic view of a system for performing one more diagnostic and/or therapeutic functions in association with cardiac tissue.

An embodiment of an ablation electrode assembly 10 is generally shown in FIG. 1. Referring now to FIG. 2, the ablation electrode assembly 10 can comprise part of an irrigated catheter system 11 for examination, diagnosis, and/or treatment of internal body tissues (e.g., targeted tissue areas 13). In an exemplary embodiment, the irrigated catheter assembly can comprise an ablation catheter 15 (e.g., radio frequency (RF), cryoablation, ultrasound, etc.). The instant disclosure generally refers to RF ablation electrodes and electrode assemblies, but it is contemplated that the instant disclosure is equally applicable to any number of other ablation electrodes and electrode assemblies where the temperature of the device and of the targeted tissue areas can be factors during diagnostic and/or therapeutic medical procedures.

Still referring to FIG. 2, the irrigated catheter assembly includes a catheter shaft 17 that is an elongate, tubular, flexible member configured for movement within a body. The catheter shaft 17 can be introduced into a blood vessel or other structure within a body 19 through a conventional introducer. The catheter shaft 17 can be steered or guided through a body to a desired location such as targeted tissue areas 13 with pullwires, tension elements, so-called push elements, or other means known in the art.

The irrigated catheter assembly further includes at least one fluid lumen or fluid delivery tube 12 disposed within the catheter shaft 17. The fluid delivery tube 12 is configured to supply fluid to the ablation electrode assembly 10. The fluid delivery tube 12 of the irrigated catheter assembly can be connected to a fluid source 21 providing a biocompatible fluid such as saline, or a medicament, through a pump 23, which can comprise, for example, a fixed rate roller pump or variable volume syringe pump with a gravity feed supply from the fluid source for irrigation. The fluid source 21 and/or pump 23 is conventional in the art. The fluid source 21 and/or pump 23 can comprise a commercially available unit sold under the name Cool Point™ available from St. Jude Medical, Inc. in an embodiment.

The irrigated catheter assembly can further include one or more positioning electrodes 51 mounted in or on the catheter shaft 17. The electrodes 51 can comprise, for example, ring electrodes. The electrodes 51 can be used, for example, with a visualization, navigation, and mapping system 25. The electrodes 51 can be configured to provide a signal indicative of both a position and orientation of at least a portion of the catheter shaft 17. The visualization, navigation, and/or mapping system 25 with which the electrodes 51 can be used can comprise an electric field-based system, such as, for example, that having the model name ENSITE NAVX (aka EnSite Classic as well as newer versions of the EnSite system, denoted as ENSITE VELOCITY) and commercially available from St. Jude Medical, Inc. and as generally shown with reference to U.S. Pat. No. 7,263,397 titled "Method and Apparatus for Catheter Navigation and Location and Mapping in the Heart," the entire disclosure of which is incorporated herein by reference. In accordance with an electric field-based system, the electrodes 51 can be configured to be responsive to an electric field transmitted within the body 19 of the patient. The electrodes 51 can be used to sense an impedance at a particular location and transmit a representative signal to an external computer or processor. In other exemplary embodiments, however, the visualization, navigation, and/or mapping system 25 can comprise other types of systems, such as, for example and without limitation: a magnetic field-based system such as the CARTO System (now in a hybrid form with impedance- and magnetically-driven electrodes) available from Biosense Webster, and as generally shown with reference to one or more of U.S. Pat. No. 6,498,944 entitled "Intrabody Measurement," U.S. Pat. No. 6,788,967 entitled "Medical Diagnosis, Treatment and Imaging Systems," and U.S. Pat. No. 6,690,963 entitled "System and Method for Determining the Location and Orientation of an Invasive Medical Instrument," the entire disclosures of which are incorporated herein by reference, or the gMPS system from MediGuide Ltd. of Haifa, Israel (now owned by St. Jude Medical, Inc.), and as generally shown with reference to one or more of U.S. Pat. No. 6,233,476 entitled "Medical Positioning System," U.S. Pat. No. 7,197,354 entitled "System for Determining the Position and Orientation of a Catheter," and U.S. Pat. No. 7,386,339 entitled "Medical Imaging and Navigation System," the entire disclosures of which are incorporated herein by reference. In accordance with a magnetic field-based system, the electrodes 51 can be configured to be responsive to a magnetic field transmitted through the body 19 of the patient. The electrodes 51 can be used to sense the strength of the field at a particular location and transmit a representative signal to an external computer or processor. The electrodes 51 can comprise one or more metallic coils located on or within the catheter shaft 17 in a magnetic field-based system. As noted above, a combination electric field-based and magnetic field-based system such as the CARTO 3 System also available from Biosense Webster, and as generally shown with reference to U.S. Pat. No. 7,536,218 entitled "Hybrid Magnetic-Based and Impedance- Based Position Sensing," the entire disclosure of which is incorporated herein by reference, can be used. In accordance with a combination electric field-based and magnetic field-based system, the electrodes 51 can comprise both one or more impedance-based electrodes and one or more magnetic coils. Commonly available fluoroscopic, computed tomography (CT), and magnetic resonance imaging (MRI)-based systems can also be used.

The irrigated catheter assembly can include other conventional components such as, for example and without limitation, conductors associated with the electrodes, and possibly additional electronics used for signal processing, visualization, localization, and/or conditioning. The irrigated catheter assembly can further include multiple lumens for receiving additional components. The irrigated catheter assembly can further include a cable connector or interface 27 and a handle 29. The cable connector or interface 27 can provide mechanical, fluid, and electrical connection(s) for cables 31, 33, 35 extending from the pump 23 and/or an ablation system 37 as described in more detail below. The cable connector or interface 27 can be conventional in the art and can be disposed at the proximal end of the irrigated catheter assembly. The handle 29 can provide a location for the clinician to hold the irrigated catheter assembly and can further provide means for steering or guiding the catheter shaft 17 within the body 19 as known in the art. Catheter handles are generally conventional in the art and it will be understood that the construction of the handle can vary. In an embodiment, for the purpose of steering the catheter shaft 17 within the body 19, the handle 29 can be substituted by a controllable robotic actuator.

Figure 3:
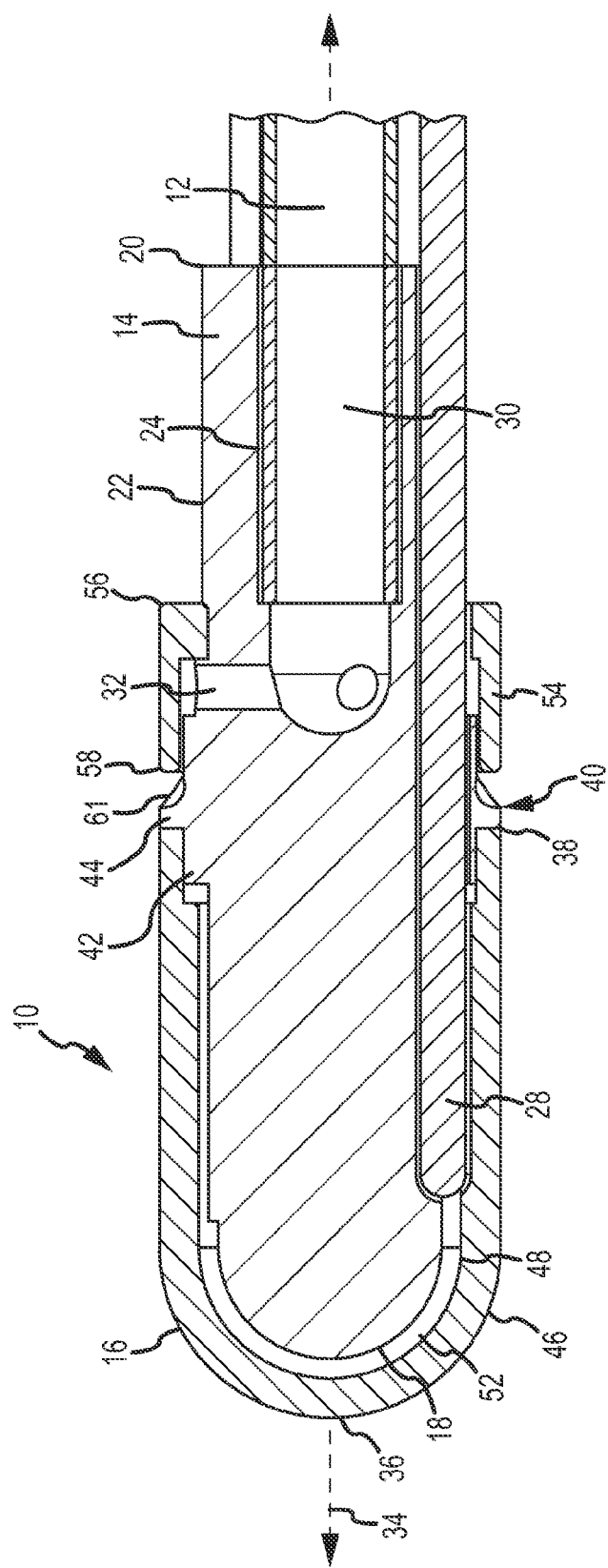
FIG. 3 is a cross-sectional view of the ablation electrode assembly of FIG. 1.

Ablation electrode assembly 10 can be connected to and/or coupled with the catheter shaft 17. Ablation electrode assembly 10 can be disposed at or near the distal end of the catheter shaft 17. Ablation electrode assembly 10 can be disposed at the extreme distal end (e.g., tip) of the catheter shaft 17. Referring now to FIGS. 1 and 3, the ablation electrode assembly 10 can include an inner core member 14 and an outer shell 16 in accordance with a first embodiment of the disclosure. The lengths and/or diameters of inner core member 14, outer shell 16, ablation electrode assembly 10, as well as portions thereof, can vary depending on the design of ablation electrode assembly 10. The outer shell 16 may be about 4 millimeters in length in an embodiment.

Inner core member 14 is provided to interrupt and/or reduce the heat transfer path through the ablation electrode assembly 10 and provide an insulated internal flow path for irrigation fluid. More particularly, inner core member 14 can be provided to interrupt and/or reduce the heat transfer path between multiple thermal sensors located within the ablation electrode assembly 10 as described in more detail below. By interrupting and/or reducing the heat transfer path between multiple thermal sensors located within the ablation electrode assembly 10, it can improve the ability of a catheter incorporating the ablation electrode assembly 10 to distinguish the higher temperature associated with lesion formation at the interface between the electrode of the ablation electrode assembly 10 and the targeted tissue.

Inner core member 14 comprises a thermal insulator having a reduced thermal conductivity. Inner core member 14 can be thermally nonconductive in accordance with an embodiment of the disclosure. Inner core member 14 can comprise an electrically nonconductive material in accordance with an embodiment of the disclosure. In general, the inner core member 14 is lower in thermal conductivity, and preferably substantially lower, than outer shell 16. Inner core member 14 can comprise a reduced thermally conductive polymer in accordance with an embodiment of the disclosure. A reduced thermally conductive polymer is one with physical attributes that decrease heat transfer by about 10% or more, provided that the remaining structural components are selected with the appropriate characteristics and sensitivities desired for the ablation electrode assembly 10. One reduced thermally conductive material can include polyether ether ketone (PEEK). Additional examples of thermally nonconductive or reduced thermally conductive materials that can be useful in conjunction with the instant disclosure include, but are not limited to, high density polyethylene (HDPE), polyimide thermoplastic resins, such as ULTEM® as provided by General Electric Plastics (now known as SABIC Innovative Plastics), polyaryletherketones, polyurethane, polypropylene, oriented polypropylene, polyethylene, crystallized polyethylene terephthalate, polyethylene terephthalate, polyester, polyetherimide, acetyl, ceramics, and/or various combinations thereof. Inner core member 14 can also comprise other plastic materials such as silicone or polyether block amides such as those sold under the trademark PEBAX® and generally available from Arkema France in other embodiments of the disclosure.

Figure 4:
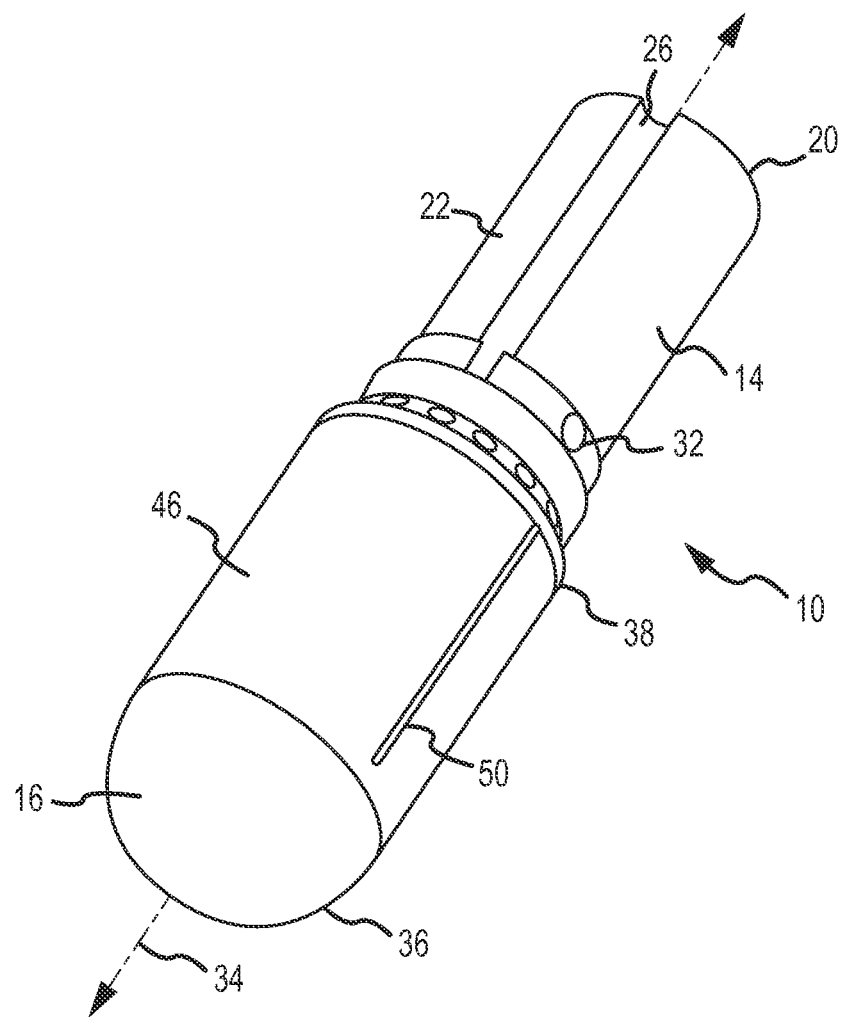
FIG. 4 is an isometric view of the ablation electrode assembly of FIG. 1.

Inner core member 14 has a distal end 18 and a proximal end 20. Inner core member 14 can be generally cylindrical in shape. The distal end 18 of the inner core member 14 can be partially spherical or generally hemispherical in shape in accordance with an embodiment of the disclosure. The proximal end 20 of the inner core member 14 can be configured for coupling and/or connecting inner core member 14 with the catheter shaft. The proximal end 20 of the inner core member 14 can also be configured to receive the fluid delivery tube 12. The inner core member 14 can include multiple lumens for receiving any number of components (e.g., wires and the like) which can be routed through the inner core member 14. As best illustrated in FIG. 3, the inner core member 14 also has an outer surface 22 and an inner surface 24. As best illustrated in FIG. 4, the outer surface 22 of the inner core member 14 includes a channel 26. The outer surface 22 of the inner core member 14 includes a plurality of channels 26 in an embodiment of the disclosure.

As best illustrated in FIGS. 1 and 3, each of the plurality of channels 26 is configured to receive a thermal sensor 28. Accordingly, the ablation electrode assembly 10 can include a plurality of thermal sensors 28 in accordance with an embodiment of the disclosure. The ablation electrode assembly 10 can include three thermal sensors 28 in accordance with an embodiment of the disclosure. The thermal sensors 28 can be substantially equally spaced around the periphery or circumference of the inner core member 14. Although three sensors that are substantially equally spaced are mentioned in detail, the ablation electrode assembly 10 can include fewer or more thermal sensors 28 in other embodiments and the location of the thermal sensors 28 can vary in other embodiments. For example, in an embodiment, a single thermal sensor 28 may be centered within the ablation electrode assembly 10. Thermal sensors 28 can be connected and/or coupled to inner core member 14 (and/or ablation electrode assembly 10) in any manner that is conventional in the art to hold thermal sensors 28 in place relative to inner core member 14 (and/or ablation electrode assembly 10). Thermal sensors 28 are configured for measurement and temperature control/regulation of ablation electrode assembly 10. Thermal sensors 28 can be any mechanism known to one of ordinary skill in the art, including for example and without limitation, thermocouples and/or thermistors. Thermal sensors 28 can comprise other types of devices, such as for example and without limitation, devices for determining pressure, temperature and a flow parameter of a flowing fluid available from Radi Medical Systems AB, and as generally shown with reference to at least U.S. Pat. No. RE39,863 entitled "Combined flow, pressure and temperature sensor," the entire disclosure of which is incorporated herein by reference.

Inner surface 24 defines an inner cavity 30 as best illustrated in FIG. 3. In an embodiment of the disclosure, the inner core member 14 includes a radially extending passageway 32 that extends from the inner cavity 30 to the outer surface 22 of the inner core member 14. Inner core member 14 includes a plurality of radially extending passageways 32 in an embodiment. Each of the radially extending passageways 32 extend from the inner cavity 30 of the inner core member 14 to the outer surface 22 of the inner core member 14. Each of the radially extending passageways 32 can be substantially centrally located on the inner core member 14 relative to a longitudinal axis 34 of the ablation electrode assembly 10. In an embodiment, the radially extending passageways 32 can be oriented at about 90 degrees relative to the longitudinal axis 34 of the ablation electrode assembly 10. In accordance with other embodiments, the radially extending passageways 32 can be angled generally toward the distal end 18 of the inner core member at an acute angle (e.g., between about 20 to about 70 degrees, and for some embodiments, between about 30 to about 65 degrees) with respect to the longitudinal axis 34 of the ablation electrode assembly 10. The orientation of the radially extending passageways 32 vary depending on the design of the ablation electrode assembly 10. The radially extending passageways 32 of the inner core member 14 can be straight or curved in various embodiments of the disclosure. In accordance with an embodiment of the disclosure, the radially extending passageways 32 of the inner core member 14 can be diametrically opposed to each other around the perimeter or circumference of the inner core member 14. The radially extending passageways 32 can be generally tubular and can have a constant diameter along their length. In an embodiment, radially extending passageways 32 can have a diameter ranging in size from about 0.008 to about 0.015 inches, and for some embodiments between about 0.010 to about 0.012 inches. Alternate configurations having various shapes and diameters, for example, along all or portions of the length of the radially extending passageways 32 can be used in various embodiments. Radially extending passageways 32 can be configured to provide proximal delivery of irrigation fluid. Delivery of irrigation fluid generally reduces char, thrombus formation, and coagulum formation, thereby enabling greater energy delivery during RF ablation. Delivery of irrigation fluid can displace blood and prevent stasis in the areas adjacent the outer shell 16 of the ablation electrode assembly 10.

Outer shell 16 improves temperature correlation between the electrode and tissue interface because it is configured as a thin shell, in place of a solid mass. The thin shell design can also mitigate temperature gradients across the ablation electrode assembly 10, as well as mitigate the effects of orientation of a catheter incorporating the ablation electrode assembly 10 in connection with monitoring the temperature of the ablation electrode assembly 10 and/or targeted tissue.

Outer shell 16 can be a thin shell (i.e., have a small thickness) and can be external to and/or surround the inner core member 14. Outer shell 16 can comprise a single layer. Outer shell 16 can be comprised of any electrically, and potentially thermally, conductive material known to those of ordinary skill in the art for the delivery of ablative energy to targeted tissue areas. Examples of electrically conductive materials include gold, platinum, iridium, palladium, stainless steel, and/or any combination thereof. In particular, a combination of platinum and iridium can be used in various combinations. Outer shell 16 can be fabricated or constructed in accordance with any method or technique known to one of ordinary skill in the art. For example and without limitation, outer shell 16 can be fabricated or constructed using so-called deep drawn metal forming techniques, metal-punching techniques, electroforming techniques (e.g., electroforming over a sacrificial form that can include rods or other internal forms that melt or are subsequently dissolved), powdered metal techniques (e.g., pressing powered metal into a slug, sintering at high heat, and then covering the pressed and sintered slug with a metallic covering member), liquid metal injection molding (MIM) techniques, and the like. The powered metal techniques can also include sacrificial members, and the pressed and sintered slug can itself conduct fluid and thermal energy inside, around, and against the metallic covering.

Outer shell 16 can be electrically connected to an ablation system 37 to allow for the delivery of ablative energy, or the like. Outer shell 16 can be electrically connected to an ablation system 37 in any manner conventional in the art. For example, a power wire 35 (best illustrated in FIG. 7) can be provided within outer shell 16 of ablation electrode assembly 10. The power wire 35 can extend through a lumen(s) provided within the ablation electrode assembly 10. The irrigated catheter assembly can be configured for operation at an initial power setting of up to 50 Watts.

The ablation system 37 can be comprised of, for example, an ablation generator 39 one or more ablation patch electrodes 41. The ablation generator 39 generates, delivers, and controls ablation energy (e.g., RF) output by the irrigated catheter assembly and the outer shell 16 of the ablation electrode assembly 10 thereof, in particular. The generator 39 is conventional in the art and can comprise a commercially available unit sold under the model number IBI-1500T RF Cardiac Ablation Generator, available from St. Jude Medical, Inc. In an exemplary embodiment, the generator 39 can include an RF ablation signal source 43 configured to generate an ablation signal that is output across a pair of source connectors: a positive polarity connector SOURCE (+), which electrically connects to the outer shell 16 of the ablation electrode assembly 10 of the irrigated catheter assembly; and a negative polarity connector SOURCE (−), can be electrically connected to one or more of the patch electrodes 41. It should be understood that the term connectors as used herein does not imply a particular type of physical interface mechanism, but is rather broadly contemplated to represent one or more electrical nodes (including multiplexed and de-multiplexed nodes). The source is configured to generate a signal at a predetermined frequency in accordance with one or more user specified control parameters (e.g., power, time, etc.) and under the control of various feedback sensing and control circuitry. The source can generate a signal, for example, with a frequency of about 450 kHz or greater for RF energy. The generator 39 can also monitor various parameters associated with the ablation procedure including, for example, impedance, the temperature at the distal tip of the irrigated catheter assembly, applied ablation energy, power, force, proximity, and the position of the irrigated catheter assembly, and provide feedback to the clinician or another component within the irrigated catheter assembly regarding these parameters. Operation in a temperature control mode can be, for example, at a set point above 50 degrees Celsius.

Outer shell 16 has a distal end 36 and a proximal end 38. Outer shell 16 can be generally cylindrical in shape. The distal end 36 of the outer shell 16 can be partially spherical or generally hemispherical in shape in accordance with an embodiment of the disclosure. The proximal end 38 of outer shell 16 can be configured for connection to the inner core member 14. Outer shell 16 can be coupled together or connected with inner core member 14 along the same longitudinal axis 34. Inner core member 14 and outer shell 16 can be connected or coupled together by any known mechanisms including, for example and without limitation, adhesive bonding, press-fit configurations, snap-fit configurations, ultrasonic staking, mechanical deformation, or any other mechanism known to one of ordinary skill in the art. In an embodiment, a connecting member 40 can be used to connect the outer shell 16 to the inner core member 14. For example, the connecting member 40 can comprise a generally annular ring 42 and a radially outwardly extending flange 44 at an axial (e.g., proximal) end of the generally annular ring 42. The generally annular ring 42 can have an outer diameter that is substantially equal to the inner diameter of the outer shell 16 at the proximal end 38 of the outer shell 16. The radially outwardly extending flange 44 of the connecting member 40 can have an outer diameter that is substantially equal to the outer diameter of the outer shell 16. At least a portion of the outer shell and the radially outwardly extending flange 44 can be connected using any of the mechanisms for connection described above. In the embodiment described above, the connecting member 40 can be separate from the remainder of the inner core member 14, such that the inner core member 14 and connecting member 40 form a multiple-piece assembly. In other embodiments, the connecting member 40 can be integral with the inner core member 14, such that the inner core member 14 and connecting member 40 form a single-piece assembly.

The outer shell 16 also has an outer surface 46 and inner surface 48 as best illustrated in FIG. 3. As best illustrated in FIG. 4, the outer surface 46 of the outer shell 16 can be scored with at least one slot 50. The outer surface 46 of the outer shell 16 can be scored with a plurality of grooves or slots 50 in accordance with an embodiment of the disclosure. Each of the plurality of grooves or slots 50 can extend axially, parallel to the longitudinal axis 34 of the ablation electrode assembly 10. Each of the plurality of grooves or slots 50 can extend from the proximal end 38 of the outer shell 16 toward the distal end 36 of the outer shell 16. Each of the plurality of grooves or slots 50 can extend for a substantial portion of the axial length of the outer shell 16. Each of the plurality of grooves or slots 50 can be configured to separate the outer shell 16 into a plurality of segments. The ablation electrode assembly 10 can include a separate, individual thermal sensor 28 for each of the plurality of segments of the outer shell 16. By separating the outer shell 16 into a plurality of segments, more complete segregation of individual thermal sensors 28 can be obtained. In an embodiment, at least one retaining wire and/or safety wire (not shown) can be extended through a lumen in the catheter shaft and can be connected to the ablation electrode assembly 10. The retaining wire and/or safety wire can be configured to ensure that that the ablation electrode assembly 10 is not separated from the catheter shaft to which it is attached during movement of the irrigated catheter assembly within a body.

Inner core member 14 and outer shell 16 define a space 52. Space 52 can further interrupt and/or reduce the heat transfer path between multiple thermal sensors 28. The configuration of the space 52 can vary greatly and can be regular or irregular and can include support members (e.g., flutes, bosses, posts, and the like) to maintain separation and a useable space between the shells. The space 52 can be configured as an annular space in accordance with an embodiment of the invention. In accordance with an embodiment of the disclosure, the space 52 can comprise a vacuum region or evacuated region. The vacuum space or evacuated region serves as an insulator, thereby reducing convection heat transfer phenomena.

In accordance with an embodiment of the disclosure, the ablation electrode assembly 10 further includes an irrigant distribution element 54. Irrigant distribution element 54 can be configured as a generally annular ring in accordance with an embodiment of the disclosure. The irrigation distribution element 54 has a proximal end 56 and a distal end 58. At least a portion of the proximal end 56 of the irrigant distribution element 54 can engage a catheter shaft in which the inner core member 14 can be located. At least a portion of the distal end 58 of the irrigant distribution element 54 can surround and/or encircle the inner core member 14 and, further, can define a circumferential irrigation port 60 between the irrigant distribution element 54 and the inner core member 14 in accordance with an embodiment of the disclosure. Irrigant distribution element 54 is configured to guide irrigation fluid toward outer shell 16 about and along outer surface 46 of the outer shell 16, and in particular, direct the fluid (e.g., irrigant) flow in a direction substantially parallel with the outer surface 46 of the outer shell 16. Irrigant distribution element 54 can include a fluid shaping member 61 that helps ensure that the fluid flow tends toward the surface 46 of the outer shell 16 of the ablation electrode assembly 10. For example and without limitation, the fluid shaping member 61 of the irrigant distribution element 54 can include a channel, rifling, boss, hump, chamfer, and/or combination thereof on a surface defining the circumferential irrigation port 60. The fluid shaping member 61 is configured to disturb fluid flow (e.g., cause fluid flowing closer to the outer surface of the inner core member 14 to slow down relative to fluid flowing farther from the outer surface of the inner core member 14), thereby helping to ensure that the fluid flow tends toward the surface 46 of the outer shell 16.

Figure 5:
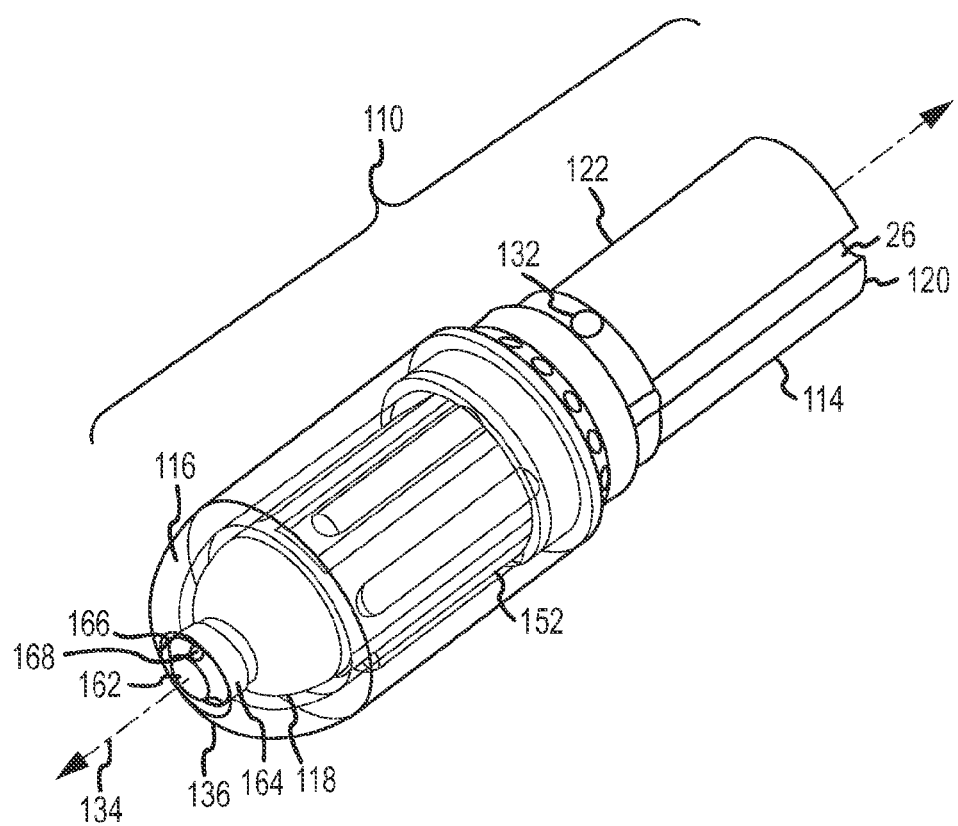
FIG. 5 is an isometric partially transparent view of an ablation electrode assembly in accordance with a second embodiment of the disclosure.
Figure 6:
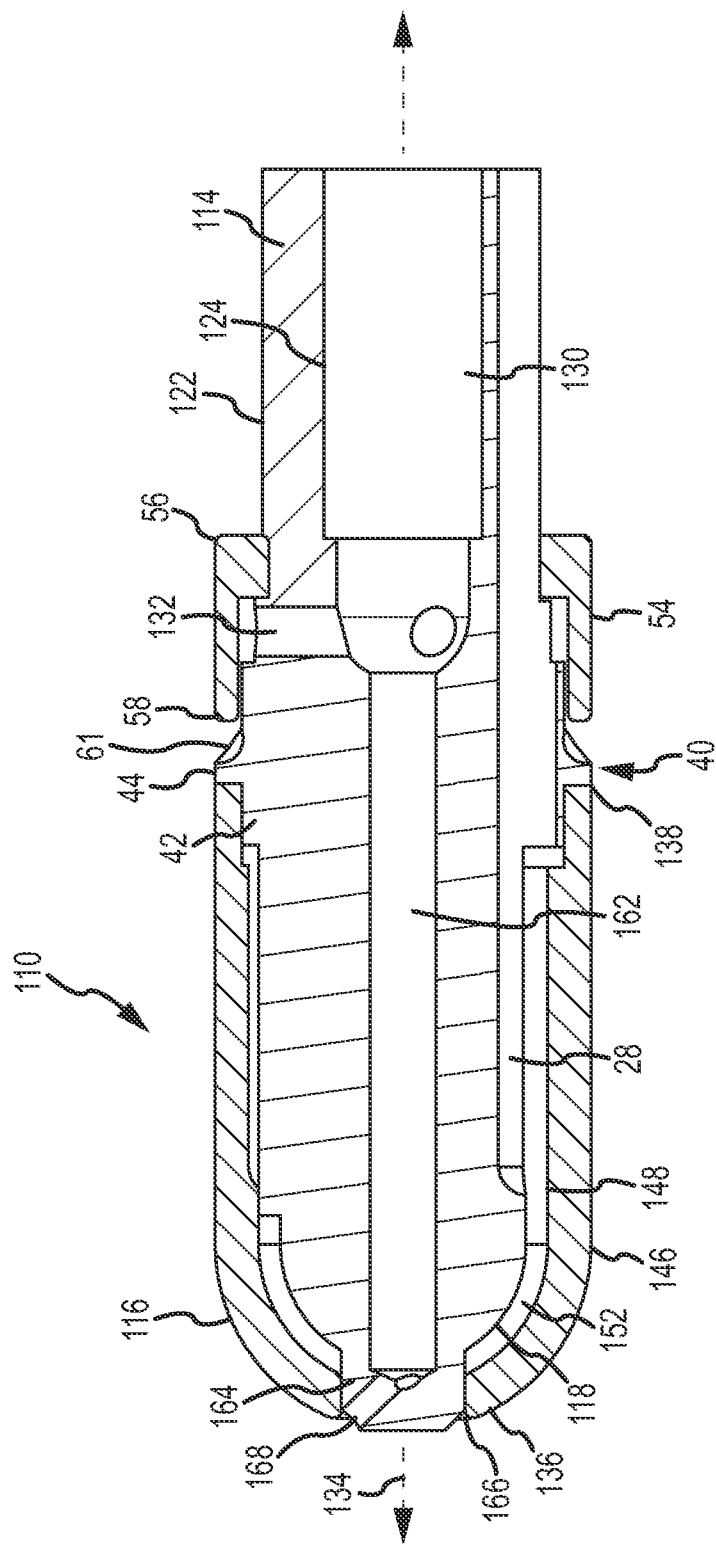
FIG. 6 is a cross-sectional view of the ablation electrode assembly of FIG. 4.

Referring now to FIGS. 5 and 6, the ablation electrode assembly 110 can include an inner core member 114 and an outer shell 116 in accordance with a second embodiment of the disclosure. The inner core member 114 and outer shell 116 of the ablation electrode assembly 110 in accordance with a second embodiment of the disclosure can be substantially identical to the inner core member 14 and outer shell 16 of the ablation electrode assembly 10 as described herein, except that the inner core member 114 and outer shell 116 can be modified to provide both proximal and distal delivery of irrigation fluid. The ablation electrode assembly 110 is configured to provide both proximal and distal delivery of irrigation fluid, can be especially beneficial to reduce thrombus formation and/or charring at the distal end (e.g., tip) of the ablation electrode assembly 110. By providing both proximal and distal delivery of irrigation fluid, it can further displace blood and prevent stasis in the areas adjacent the outer shell 116 of the ablation electrode assembly 110.

Ablation electrode assembly 110 is configured for distal delivery of irrigation fluid with an axially extending passageway 162 extending from the inner cavity 130 of the inner core member 114 to the distal end 118 of the inner core member 114. The inner core member 114 can further include a distal end portion 164 and the outer shell 116 can include an aperture 166 at distal end 136 of the outer shell 116. The distal end portion 164, coupled with aperture 166, can enable irrigation fluid flowing through the axially extending passageways 162 to flow to a distal end 136 (e.g., tip) of outer shell 116, therein substantially irrigating the distal end 136 (e.g., tip) of outer shell 116 of the ablation electrode assembly 110. Outer shell 16, 116 does not include any radially extending aperture in accordance with an embodiment of the disclosure. Distal end portion 164 can extend distally from the partially spherical and/or generally hemispherical distal end 118 of the inner core member 114 and can be generally cylindrical in shape. Distal end portion 164 can extend within the aperture 166 at distal end 136 of the outer shell 116. Distal end portion 164 can include one or more ports 168 extending from the axially extending passageway 162. For example and without limitation, distal end portion 164 can include three ports. Each of the ports 168 can be oriented at an acute angle (e.g., about 45 degrees) relative to the longitudinal axis 134 of the ablation electrode assembly 110. The orientation of the ports 168 varies depending on the design of the ablation electrode assembly 110. The ports 168 may be substantially equally spaced around the circumference of the distal end portion 164 in an embodiment. The axially extending passageway 162 extends through the distal end portion 164. Distal end portion 164 can comprise the same material as the inner core member 114. In other embodiments, the axially extending passageway 162 can extend directly through the distal end 36 of the outer shell 116.

In an embodiment of the disclosure, a coating (not shown) can be disposed on at least a portion of the inner core member 114 and/or outer core member 116 that defines the axially extending passageway 162. The coating can be comprised of an electrically nonconductive material. The coating can be comprised of diamond, diamond-like carbon (DLC) or polytetrafluoroethylene (PTFE), which is commonly sold by the E. I. du Pont de Nemours and Company under the trade name Teflon®. In an embodiment, the coating can be provided around the entire circumference and along the entire length of the axially extending passageway 162. However, the coating can be provided only around a portion of the circumference and/or only around a portion of the length of the axially extending passageway 162 in accordance with various embodiments of the disclosure. The amount of the coating provided around the circumference and/or length of the axially extending passageway 162 or portion thereof can vary depending on the relative requirements of ablation electrode assembly 110.

Figure 7:
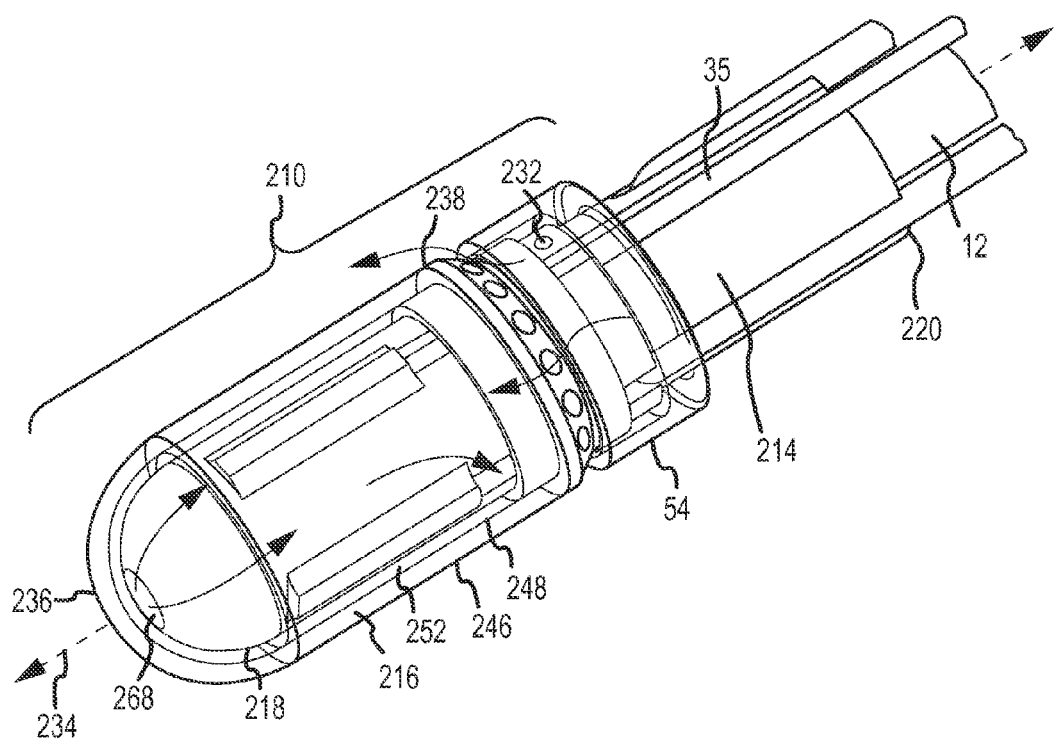
FIG. 7 is an isometric partially transparent view of an ablation electrode assembly in accordance with a third embodiment of the disclosure.
Figure 8:
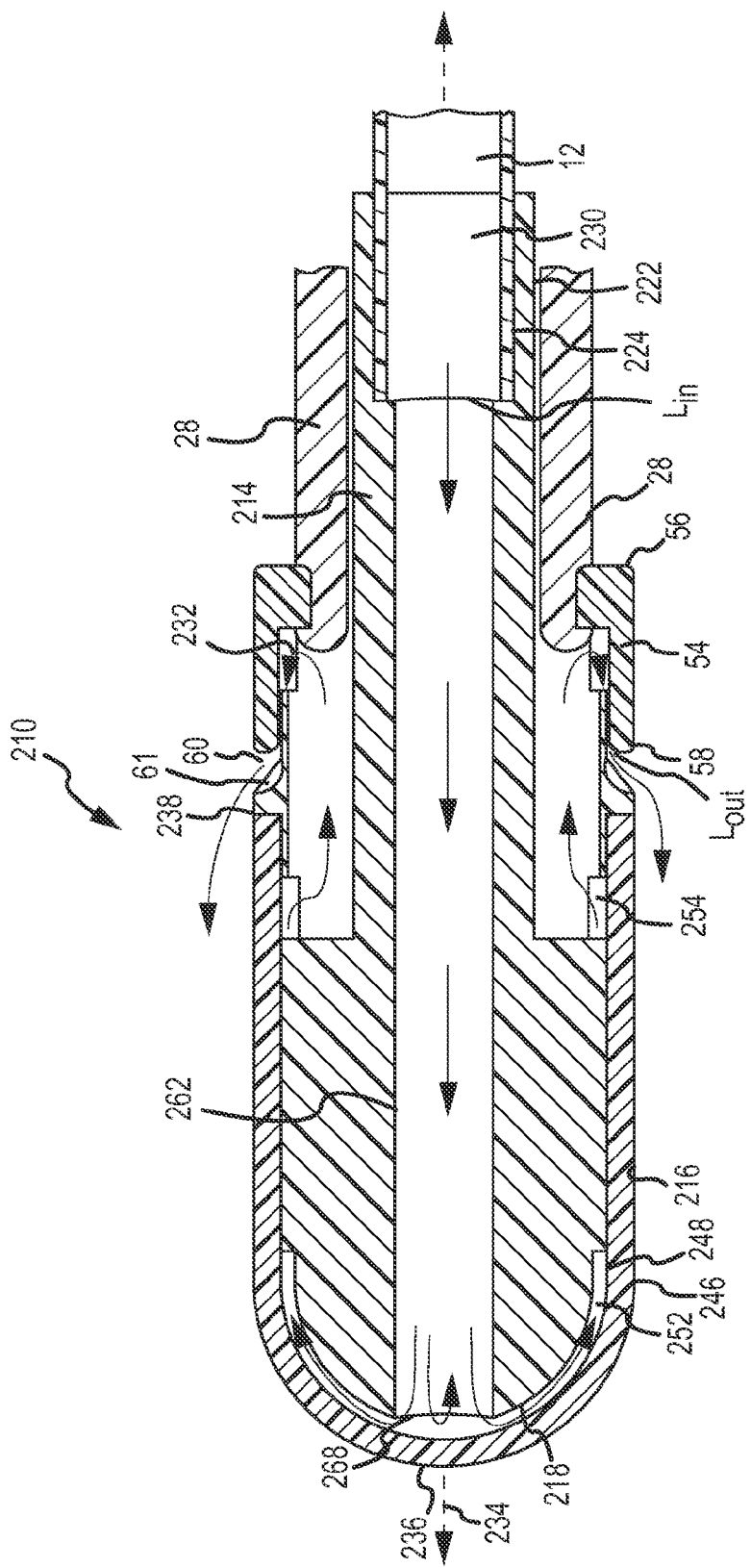
FIG. 8 is a cross-sectional view of the ablation electrode assembly of FIG. 7.

Referring now to FIGS. 7 and 8, the ablation electrode assembly 210 can include an inner core member 214 and an outer shell 216 in accordance with a third embodiment of the disclosure. The inner core member 214 and outer shell 216 of the ablation electrode assembly 210 in accordance with a third embodiment of the disclosure can be substantially identical to the inner core member 14 and outer shell 16 of the ablation electrode assembly 10 in accordance with a first embodiment of the disclosure as described herein, except that the inner core member 214 and outer shell 216 can be modified to allow for the flow of irrigation fluid in the annular space 252 between the inner core member 214 and outer shell 216.

Ablation electrode assembly 210 is configured for allowing the flow of irrigation fluid in the annular space 252 between the inner core member 214 and the outer shell 216 by including an aperture 268 located at the distal end 218 of the inner core member 214. The inner core member 214 also includes an axially extending passageway 262. The fluid delivery tube 12 can be in fluid communication with the axially extending passageway 262. The axially extending passageway 262 can terminate at aperture 268 located at the distal end 218 of the inner core member. Irrigation fluid from the axially extending passageway 262 can flow out of the aperture 268 in a first direction toward the distal end 236 of the outer shell 216. The irrigation fluid can then flow radially outwardly from the aperture 268 and can then eventually flow back in a second direction (i.e., opposite the first direction) toward the proximal end 238 of the outer shell 216 in the annular space 252 between the outer shell 216 and the inner core member 214. Irrigation fluid flowing in the annular space 252 can absorb heat from both the circulating blood pool and the lesion being created in the targeted tissue during RF ablation. The irrigation fluid can then exit the annular space 252 between the outer shell 216 and the inner core member 214 and can flow through a collection channel 254 and then flow through a first radially extending passageway 232 of the inner core member 214. The first radially extending passageway 232 of the inner core member 214 can be similar to radially extending passageway 32 of inner core member 14, 114, except that the first radially extending passageway 232 cannot extend from the inner cavity 30 to the outer surface 22 of the inner core member 214. The first radially extending passageway 232 of the inner core member 214 instead extends from the collection channel 254 (and thus, the annular space 252), thereby allowing irrigation fluid that has flowed through the annular space 252 to exit the ablation electrode assembly 210. Delivery of irrigation fluid generally reduces char, thrombus formation, and coagulum formation, thereby enabling greater energy delivery during RF ablation. Delivery of irrigation fluid can also displace blood and prevent stasis in the areas adjacent the outer shell 216 of the ablation electrode assembly 210.

Accordingly, the annular space 252 is in fluid communication with both the inner cavity 230 of the inner core member 214 (e.g., through the axially extending passageway 262), as well as the first radially extending passageway 232. In an embodiment where the ablation electrode assembly 210 further includes irrigant distribution element 54, the distal end 58 of irrigant distribution element 54 can define a circumferential irrigation port 60 between the irrigant distribution element 54 and the inner core member 214. Irrigation fluid exiting the first radially extending passageway 232 can flow out the circumferential irrigation port 60 as best illustrated in FIG. 8.

Figure 9:
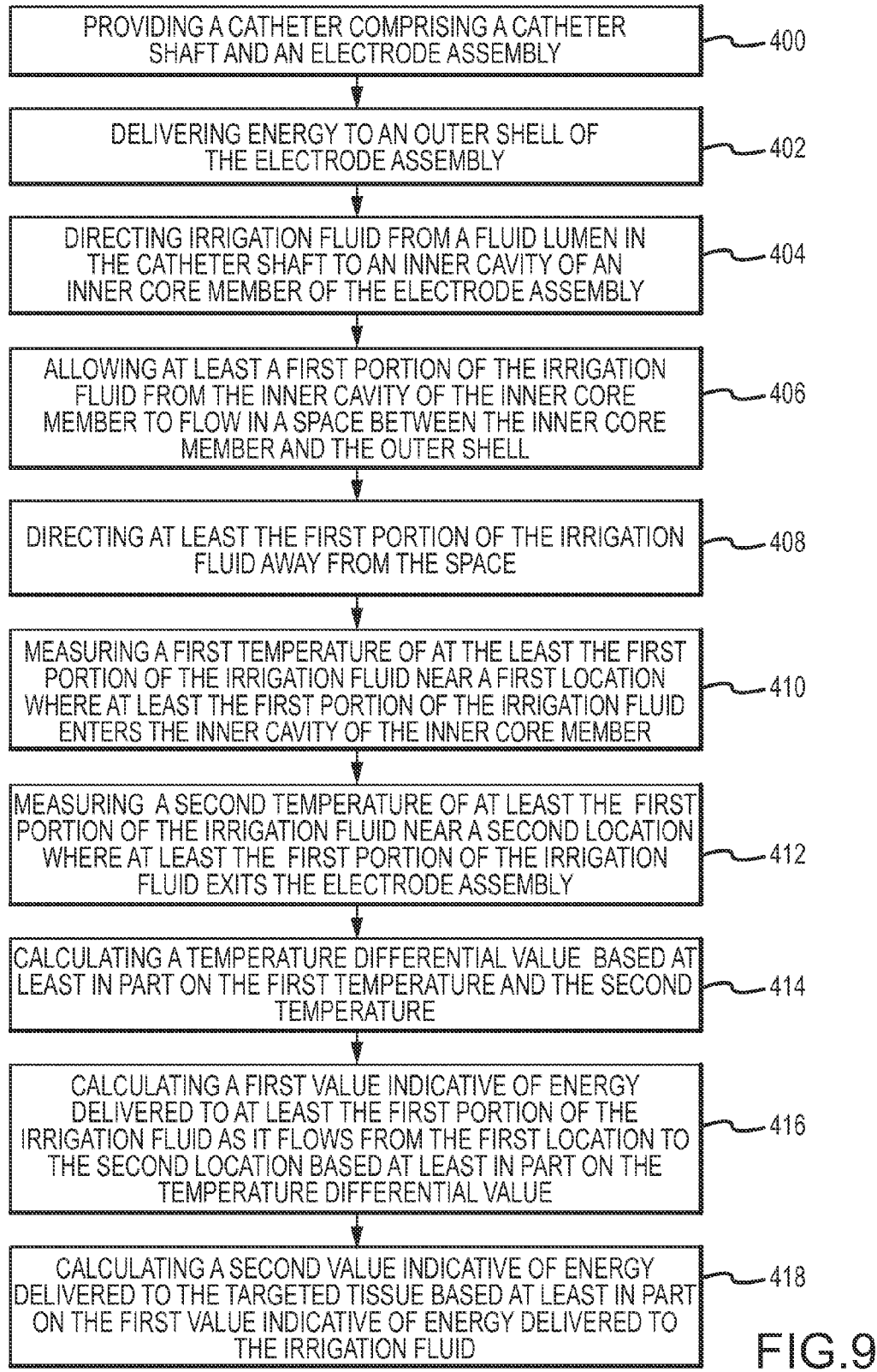
FIG. 9 is a flow diagram generally representing an exemplary method of using an ablation electrode assembly to control temperature during cardiac ablation of targeted tissue in accordance with a first embodiment of the disclosure.

FIG. 9 is a flow diagram generally representing an exemplary method of using an ablation electrode assembly 210 (or 310 as described hereinbelow) to provide irrigation fluid and/or control temperature during cardiac ablation of targeted tissue. In an embodiment of providing irrigation fluid during cardiac ablation of targeted tissue, a catheter is used in Step 400. The catheter can comprise a catheter shaft having a fluid lumen or fluid delivery tube 12 and an electrode assembly 210, 310 connected to the catheter shaft. The electrode assembly 210, 310 can include an inner core member 214, 314 having a distal end 218, 318 and a proximal end 220, 320. The inner core member 214, 314 can include an outer surface 222, 322 and an inner surface 224, 324. The inner surface can define an inner cavity 230, 330. The inner core member 214, 314 can further include a first radially extending passageway 232, 332 that extends through the outer surface 222 of the inner core member 214. The inner core member 214, 314 can further include an axially extending passageway 262, 362 extending from the inner cavity 230, 330 to the distal end 218, 318 of the inner core member 214, 314. The electrode assembly 210, 310 can further include an outer shell 216, 316 surrounding the inner core member 214, 314. The outer shell 216, 316 can have a distal end 236, 336 and a proximal end 238, 338. The ablation electrode assembly 210, 310 can further include plurality of thermal sensors 28. In an embodiment, the outer shell 216 can be scored with a plurality of axially extending grooves or slots 50 to separate the outer shell 216, 316 into a plurality of circumferentially-extending segments. In this embodiment, there can be a thermal sensor 28 for each of the plurality of segments of the outer shell 216, 316. Accordingly, each of the plurality of segments of the outer shell 216, 316 can have at least one corresponding thermal sensor 28 out of the plurality of thermal sensors 28. The inner core member 214, 314 and the outer shell 216, 316 can define an annular space 252, 352. Energy is delivered to the outer shell 216, 316 of the electrode assembly 210, 310 in Step 402. In particular, the outer shell 216, 316 of the electrode assembly 210, 310 is electrically connected to an ablation system 37 including an ablation generator 39 for generating and delivering energy to the catheter. The energy generated and delivered to the catheter 15 from the ablation generator 39 can be based at least in part on the highest temperature measurement from the plurality of thermal sensors 28 utilized in connection with the ablation electrode assembly 210, 310, both in embodiments where the outer shell 216, 316 is not separated into a plurality of segments and in embodiments where the outer shell 216, 316 is separated into a plurality of segments.

Irrigation fluid is directed from the fluid lumen or fluid delivery tube 12 to the inner cavity 30 of the inner core member 214, 314 in Step 404. At least a first portion of the irrigation fluid is allowed to flow from the inner cavity 30 of the inner core member 214, through the axially extending passageway 262 in the inner core member 214, and into the annular space 252 between the inner core member 214 and the outer shell 216 in Step 406. In accordance with one embodiment of the disclosure as generally illustrated in FIGS. 7 and 8, all of the irrigation fluid from the inner cavity 230 of the inner core member 214 (and thus all of the irrigation fluid delivered by the fluid delivery tube 12) can be directed from the inner cavity 230, through the axially extending passageway 262, and into the annular space 252. In accordance with other embodiments of the disclosure as generally illustrated in FIGS. 10 and 11, only a portion (i.e., a first portion) of the irrigation fluid from the inner cavity 30 of the inner core member 314 (and thus only a portion of the irrigation fluid delivered by the fluid delivery tube 12) can be directed from the inner cavity 330, through the axially extending passageway 362, and into the annular space 352.

At least the first portion of the irrigation fluid from the inner cavity 230, 330 of the inner core member 214, 314 is directed away from the annular space 252, 352 between the inner core member 214, 314 and the outer shell 216, 316 in Step 408. As described above, in some embodiments all of the irrigation fluid from the inner cavity 230, 330 of the inner core member 214 can be directed into the annular space 252, 352, and so all of the irrigation fluid from the inner cavity 230, 330 of the inner core member 214, 314 can be directed from the annular space 252 in Step 408. In other embodiments, only a portion (i.e., a first portion) of the irrigation fluid from the inner cavity 230, 330 of the inner core member 214, 314 (and thus only a portion of the irrigation fluid delivered by the fluid delivery tube 12) can be directed away from the annular space 252, 352. In some embodiments, the first portion of the irrigation fluid is directed away from the annular space 252, 352 to the first radially extending passageway 232, 332. In other embodiments, the first portion of the irrigation fluid is directed away from the annular space 252, 352 toward a proximal end of the catheter for elimination from the catheter at a location that is remote from a patient.

Figure 10:
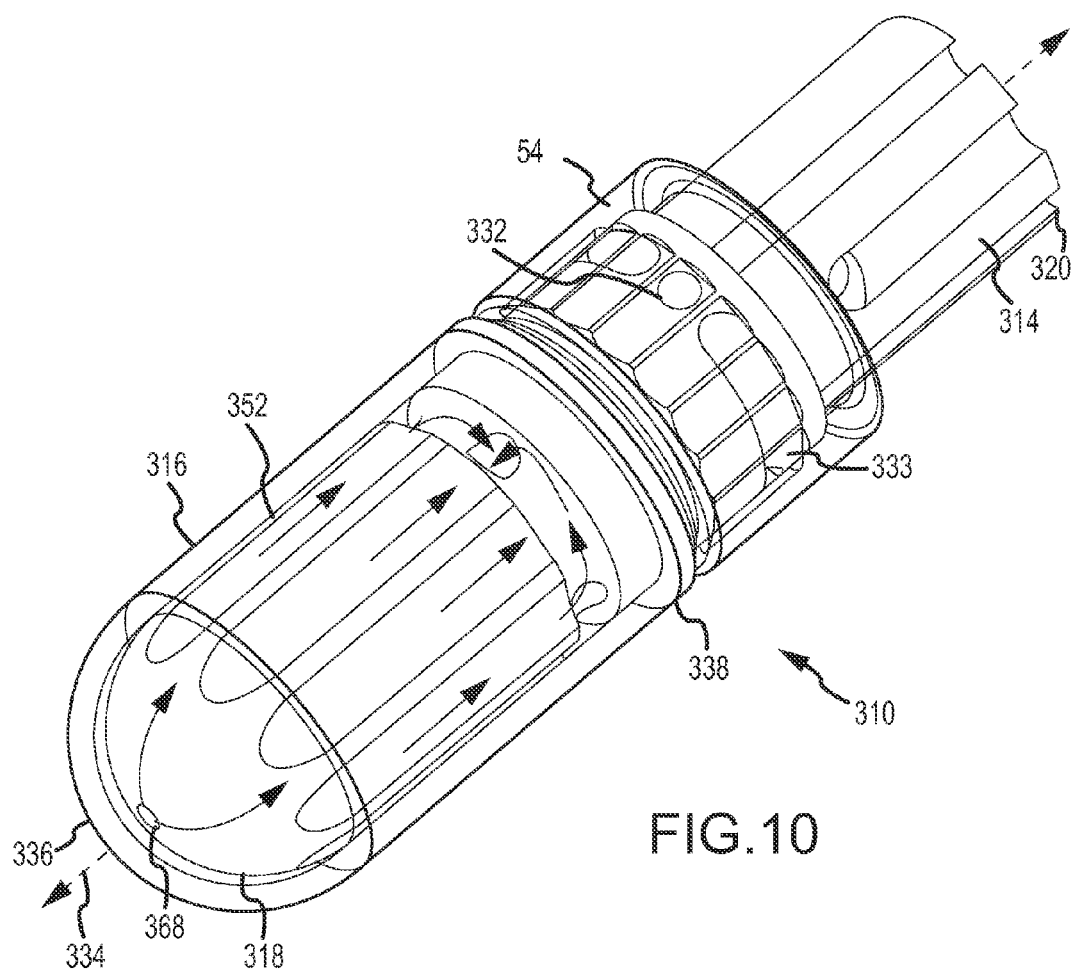
FIG. 10 is an isometric partially transparent view of an ablation electrode assembly in accordance with a fourth embodiment of the disclosure.
Figure 11:
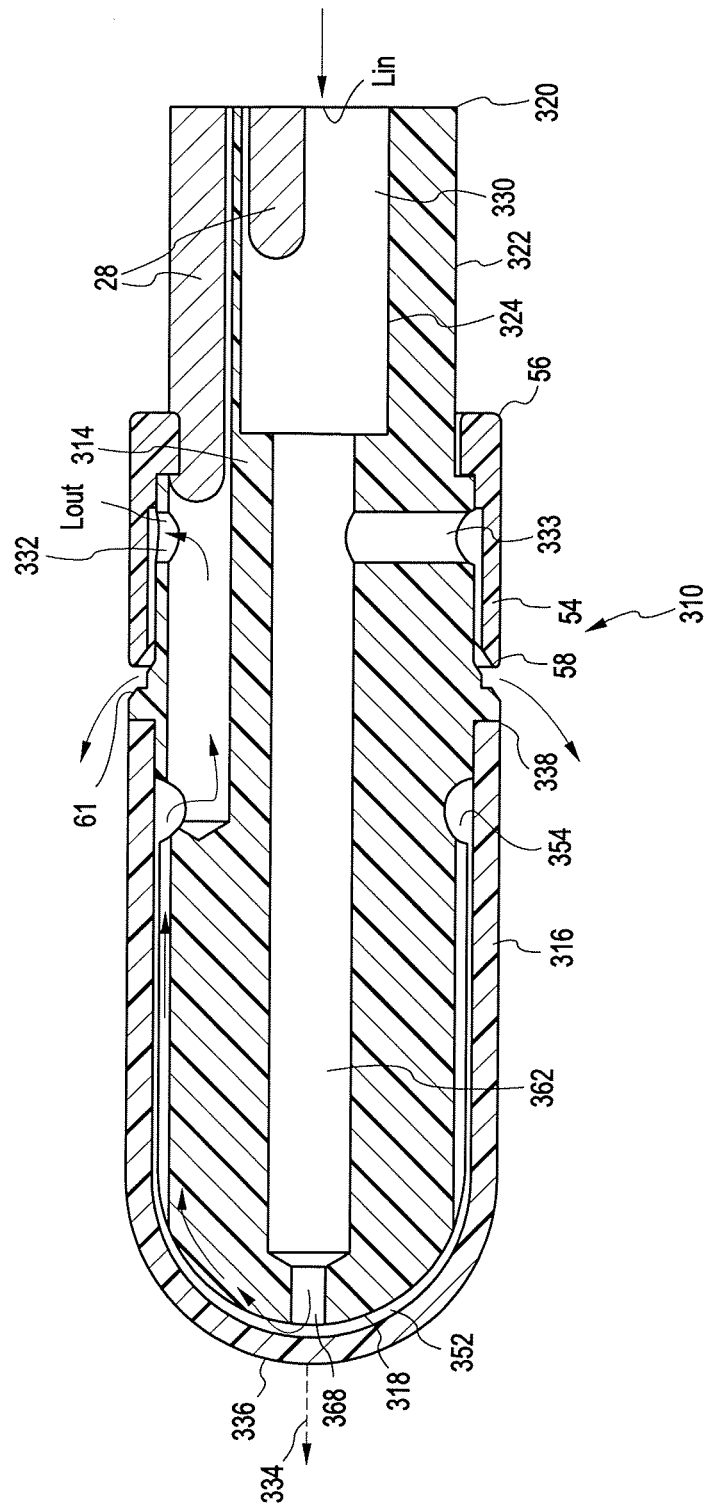
FIG. 11 is a cross-sectional view of the ablation electrode assembly of FIG. 7.

In the embodiments where only a portion (i.e., a first portion) of the irrigation fluid from the inner cavity 230, 330 of the inner core member 214, 314 is directed to the annular space 252, 352 and to the first radially extending passageway 232, 332 or toward the proximal end of the catheter for elimination from the catheter at a location that is remote from a patient, the inner core member 214, 314 includes a second radially extending passageway 333 as illustrated in FIGS. 10 and 11. The second radially extending passageway 333 extends from and is in direct fluid communication with the inner cavity 330 to the outer surface 322 of the inner core member 314. The second radially extending passageway 333 of the inner core member 314 can be similar to radially extending passageway 32, 132 of inner core member 14, 114. In accordance with this embodiment of the disclosure as generally illustrated in FIGS. 10 and 11, fluid that has flowed through the axially extending passageway 362 and/or the annular space 352 does not flow through the second radially extending passageway 333 and instead flows through the first radially extending passageway 332 as described hereinabove. At least another portion (i.e., a second portion) of the irrigation fluid from the inner cavity 330 of the inner core member 314 can be directed directly to the second radially extending passageway 333, thereby allowing for proximal delivery of irrigation fluid. Delivery of irrigation fluid generally reduces char, thrombus formation, and coagulum formation, thereby enabling greater energy delivery during RF ablation. Delivery of irrigation fluid can also displace blood and prevent stasis in the areas adjacent the outer shell 316 of the ablation electrode assembly 310. The first portion of the irrigation fluid (i.e., the portion of irrigation fluid that is directed to the annular space 352 and to the collection channel 354 and to the first radially extending passageway 332) can be separate from the second portion of the irrigation fluid (i.e., the portion of irrigation fluid that is directed to the second radially extending passageway 333).

The irrigation fluid flowing in the annular space 252, 352 can absorb heat from the circulating blood pool and the lesion being developed at the targeted tissue during RF ablation in which energy is delivered to the outer shell 216, 316 of the electrode assembly 210, 310. By monitoring the change in temperature of the irrigation fluid as it flows through the annular space 252, 352, it can be possible to estimate the energy removed from the ablation electrode assembly 210, 310 during an ablation cycle, thereby making it possible to better estimate the energy actually delivered to the targeted tissue.

In accordance with the embodiment of the ablation electrode assembly 310 generally illustrated in FIGS. 10 and 11, the flow rate of the second portion of the irrigation fluid (i.e., the portion of irrigation fluid that is directed to the second radially extending passageway 333) can be greater than the flow rate of the first portion of the irrigation fluid (i.e., the portion of irrigation fluid that is directed to the annular space 352 and to the collection channel 354 and to the first radially extending passageway 332). For example and without limitation, the flow rate of irrigation fluid from the fluid delivery tube 12 can be approximately 6-10 ml/minute, and the flow rate of the first portion of the irrigation fluid can be only approximately 1-3 ml/minute. In particular, aperture 368 can be configured to allow a flow rate for irrigation fluid of approximately 1-3 ml/minute. Accordingly, the majority of the irrigation fluid delivered by the fluid delivery tube 12 can be directed out of the second radially extending passageway 333. The flow rate of the second portion of the irrigation fluid can be approximately 3-9 ml/minute. Although these flow rates are mentioned in detail, the various flow rates can be greater or smaller in accordance with other embodiments of the disclosure. In this way, only a relatively small amount of irrigation fluid from the fluid delivery tube 12 is directed through the outer shell 316 of the ablation electrode assembly 310, while the majority of the irrigation fluid from the fluid delivery tube 12 is ejected out of the irrigant distribution element 54. Accordingly, ablation electrode assembly 310 allows for the additional steps of measuring temperatures of at least a first portion of the irrigation fluid as described in more detail below, while providing a higher secondary flow rate of irrigation fluid that is sufficient to flush the surface of the ablation electrode assembly 310 and displace blood at the lesion site in the targeted tissue. Irrigation fluid directed to the second radially extending passageway 333 with the irrigant distribution element 54 can help reduce charring and inhibit the formation of coagulum and/or soft thrombus by mixing, displacing and/or diluting blood that can be in contact with ablation electrode assembly 310.

In some embodiments, the overall total fluid volumes associated with the flow rate of the first portion of the irrigation fluid combined with the flow rate of the second portion of the irrigation fluid can be much lower than prior art or typically utilized in clinical practice. That is, overall total fluid volume can range from low single digits to less than about two or so milliliters per minute while effectively reducing or eliminating char and coagulum and improving temperature correlation for more precise control of temperature during ablation procedures. In an embodiment, overall total fluid volume delivered to a patient can be well below about seven or so milliliters per minute or less. Such low overall total fluid volumes can be especially valuable for patients already suffering from fluid overload (e.g., patient having heart failure and the like). Of course, for patients that can tolerate fluid intake or for procedures seeming to require higher fluid delivery rates or volumes, the embodiments herein can accommodate same.

A first temperature $T_{in}$ of at least the first portion of the irrigation fluid is measured at a first location $L_{in}$ near where at least the first portion of the irrigation fluid enters the inner cavity 230, 330 of the inner core member 214, 314 and/or where at least the first portion of the irrigation fluid enters the axially extending passageway 262, 362 from the inner cavity 230, 330 in Step 410. A first thermal sensor 28 is used to measure the first temperature $T_{in}$. A second temperature $T_{out}$ of at least the first portion of the irrigation fluid is measured at a second location $L_{out}$ near where at least the first portion of the irrigation fluid exits the electrode assembly 210, 310 in Step 412. In one embodiment, the second location can be near where at least the first portion of the irrigation fluid exits the radially extending passageway 232, 332. In other embodiments, the second location can be near where at least the first portion of the irrigation fluid exits the electrode assembly 210, 310 for eventual elimination from the catheter at a location remote from a patient. A second thermal sensor 28 is used to measure the second temperature $T_{out}$.

A temperature differential value $\Delta T$ is calculated based at least in part on the first temperature $T_{in}$ and the second temperature $T_{out}$ in Step 414. An electronic control unit (ECU) 45 can be in connection with the thermal sensors 28 and can be used to calculate the temperature differential value. A display device 47 can also be used in connection with the ablation electrode assembly 210, 310 and ECU 45. The ECU 45 preferably comprises a programmable microprocessor or microcontroller, but can alternatively comprise an application specific integrated circuit (ASIC). The ECU 45 can include a central processing unit (CPU) and an input/output (I/O) interface through which the ECU 45 can receive input data (e.g., temperature measurements from thermal sensors 28) and can generate output data (e.g., temperature differential value $\Delta T$). The temperature differential value $\delta T$ is calculated in accordance with the following equation:

$$\Delta T = (T_{out} - T_{in}) \qquad \text{(Equation 1)}$$

A first value $Q_1$ indicative of energy delivered to at least the first portion of the irrigation fluid as it flows from the first location (i.e., where the irrigation fluid enters the inner cavity 230, 330 of the inner core member 214, 314 and/or where the irrigation fluid enters the axially extending passageway 262, 326 from the inner cavity 230, 330) to the second location (i.e., where the irrigation fluid exits the radially extending passageway 232, 332) is calculated based at least in part on the temperature differential value $\Delta T$ in Step 416. The ECU 45 can be used to calculate the first value $Q_1$. The first value $Q_1$ is calculated in accordance with the following equation, where m=mass of the irrigation fluid and Cp=specific heat of the irrigation fluid.

$$Q_1 = mCp(T_{out} - T_{in}) \qquad \text{(Equation 2)}$$

The catheter 15 to which the ablation electrode assembly 210, 310 can be connected can include a memory such as an EEPROM that stores numerical values for the coefficient (e.g., specific heat of the irrigation fluid referred to as Cp in Equation 2) or stores a memory address for accessing the numerical values in another memory location (either in the catheter EEPROM or in another memory). The ECU 45 can also have a memory. The ECU 45 can retrieve these values or addresses directly or indirectly from the memory of the catheter 15 or the ECU 45. The input data and output data acquired and generated by the ECU 45 can also be stored in the memory of the catheter 15 or the ECU 45. As described above, the input data can include the first and second temperatures $T_{in}$ and $T_{out}$ obtained by the thermal sensors 28. The input data can further include information regarding the flow rate of irrigation fluid obtained from a control system 49 and described in more detail below. The flow rate can be used to obtain information regarding the mass of the irrigation fluid referred to as m in Equation 2. As described above, the output data can include the temperature differential value $\Delta T$ and/or the first value $Q_1$.

A second value $Q_2$ indicative of energy delivered to the targeted tissue is calculated based at least in part on the first value $Q_1$ in Step 418. The ECU 45 can be used to calculate the second value $Q_2$. The second value $Q_2$ is calculated in accordance with the following equation, where E=electrical energy provided to the ablation electrode assembly 210, 310 (E=P×t, where P=power and t=time):

$$Q_2 = E - Q_1 \qquad \text{(Equation 3)}$$

The output data can further include the second value $Q_2$. The delivery of energy to ablation electrode assembly 210, 310 is preferably controlled by the control system 49. The control system 49 is configured to determine the temperature of the tissue to be ablated and/or an appropriate ablation technique. The outer shell 216, 316 of the ablation electrode assembly 210, 310 is connected to the control system 49 with wires. The ablation generator 39 can form part of the control system 49 or can be separate from the control system 49 in other embodiments. Thermal sensors 28 are also connected to the control system. For example and without limitation, wires can extend through lumens in the catheter. Devices for determining pressure, temperature, and a flow parameter of a flowing fluid available from Radi Medical Systems AB, and as generally shown with reference to at least U.S. Pat. No. RE39,863 entitled "Combined flow, pressure and temperature sensor," the entire disclosure of which is incorporated herein by reference can be used to monitor and/or control the quantity of flow of irrigation fluid within or from the catheter at one or more locations using a flow-from pressure algorithm. These devices for determining pressure, temperature, and a flow parameter of a flowing fluid are also connected to the control system. The ECU 45 and display device 47 can also be connected to the control system 49.

The control system 49 can be configured to adjust the amount of energy E generated and delivered to the catheter 15 from the ablation generator 39 based at least in part on the temperature differential value $\Delta T$ in accordance with an embodiment of the disclosure. For example, a greater temperature differential value $\Delta T$ suggests that more energy is being removed from the ablation electrode assembly 210, 310, such that the ablation generator 39 can be configured to provide more energy to the ablation electrode assembly 210, 310. The energy provided to the ablation electrode assembly 210, 310 can be increased by increasing the power and/or the length of time of energy delivery (e.g., frequency and/or operating time) during the ablation cycle. For example, a lower temperature differential value $\Delta T$ suggests that less energy is being removed from the ablation electrode assembly 210, 310, such that the ablation generator 39 can be configured to provide less energy to the ablation electrode assembly 210, 310. The energy provided to the ablation electrode assembly 210, 310 can be decreased by decreasing the power and/or length of time of energy delivery (e.g., frequency and/or operating time) during the ablation cycle.

The temperature differential value $\Delta T$ for the irrigation fluid can be correlated to the actual temperature of the targeted tissue during RF ablation, and data regarding the correlation between the temperature differential value $\Delta T$ and the actual temperature of the targeted tissue can be stored by the ECU 45 or memory of catheter 15. The correlation between the temperature differential value $\Delta T$ and the actual temperature of the targeted tissue can be determined by utilization of the thermal properties and flow rates of the irrigation fluid to obtain information regarding the energy state of the external environment (i.e., the targeted tissue). In this way, the control system 49 can be configured to use the temperature differential value $\Delta T$ for the irrigation fluid in order to estimate the temperature of the targeted tissue 13 (or the interface between the ablation electrode assembly 210, 310 and the targeted tissue 13) and ultimately select an appropriate ablation technique. The ablation technique that is selected can be selected to produce a certain, predetermined temperature in the targeted tissue 13 that will form a desired lesion in the targeted tissue. While the desired lesion can be transmural in some embodiments, the characteristics of the desired lesion can vary significantly. The certain, predetermined temperature in the targeted tissue 13 that will form a desired lesion in the targeted tissue 13 can be affected by the thermal response of the targeted tissue. The thermal response of the targeted tissue 13 can be affected by a number of variables including tissue thickness, amount of fat and muscle, blood flow through the region, and blood flow at the interface of the ablation electrode assembly 210, 310 and the targeted tissue 13.

Figure 12:
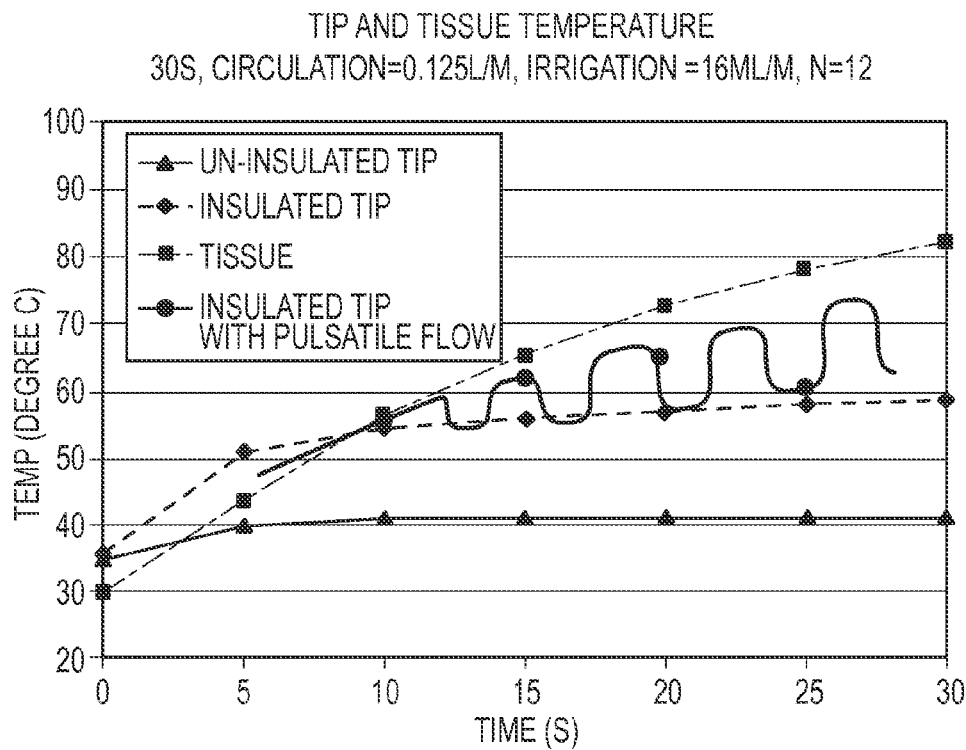
FIG. 12 is a flow diagram generally representing an exemplary method of using an ablation electrode assembly to control temperature during cardiac ablation of targeted tissue in accordance with a second embodiment of the disclosure.

FIG. 12 is an exemplary chart comparing the temperature of the distal end (i.e., tip) of ablation electrode assemblies with the temperature of the targeted tissue over time. As generally illustrated in FIG. 12, the temperature recorded at the distal end (i.e., tip) of ablation electrode assemblies typically lags that of the targeted tissue. Moreover, the temperature recorded at the distal end (i.e., tip) of ablation electrode assemblies plateaus, resulting in an even more significant difference from the temperature of the targeted tissue. Difference between the temperature recorded at the distal end (i.e., tip) of ablation electrode assemblies and targeted tissue is most acute in connection with ablation electrode assemblies that are un-insulated. Although ablation electrode assemblies having an insulated tip (including ablation electrode assemblies 10, 110, 210, 310) have an improved correlation between the temperatures of the distal end (i.e., tip) of the ablation electrode assemblies 10, 110, 210, 310 with the temperatures of the targeted tissues as generally illustrated in FIG. 12, RF ablation would benefit from an even more improved correlation between the temperatures of ablation electrode assemblies and targeted tissues.

Figure 13:
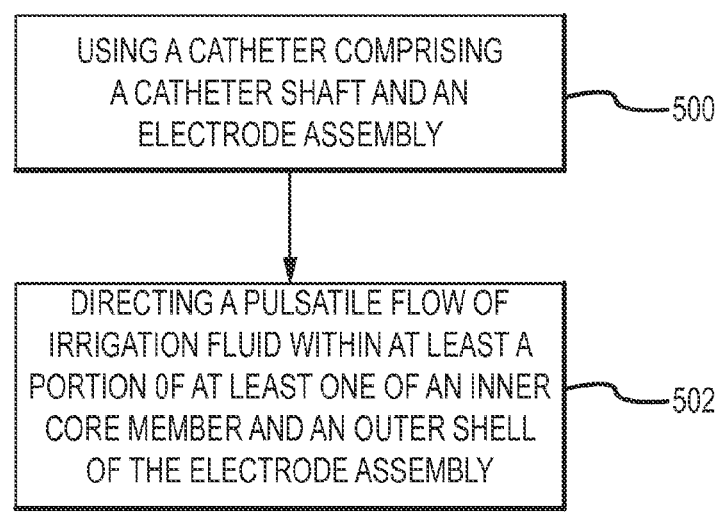
FIG. 13 is a chart comparing the temperature of the distal end (i.e., tip) of ablation electrode assemblies and the temperature of the targeted tissue over time.

FIG. 13 is a flow diagram generally representing an exemplary method of using an ablation electrode assembly 10, 110, 210, 310 to provide irrigation fluid during cardiac ablation of targeted tissue in an effort to further improve the correlation between the temperatures of the distal ends (i.e., tips) of ablation electrode assemblies 10, 110, 210, 310 and the targeted tissues. In particular, a pulsatile flow of irrigation fluid can be utilized to increase flow turbulence and help prevent stagnation areas. Although pulsatile flow is mentioned in detail in accordance with some embodiments of the invention, ablation electrode assemblies 10, 110, 210, 310 can be used in connection with any type of flow of irrigation fluid. For example and without limitation, pulsatile flow, intermittent flow, constant flow, and/or variable flow of irrigation fluid can be used in connection with ablation electrode assemblies 10, 110, 210, 310.

In an embodiment of providing irrigation fluid during cardiac ablation of targeted tissue, a catheter is used in Step 500. The catheter 15 can comprise a catheter shaft 17 having a fluid lumen or fluid delivery tube 12 and an electrode assembly 10, 110, 210, 310 connected to the catheter shaft. The electrode assembly 10, 110, 210, 310 can include an inner core member 14, 114, 214, 314 and an outer shell 16, 116, 216, 316. The inner core member 14, 114, 214, 314 and the outer shell 16, 116, 216, 316 can define an annular space 52, 152, 252, 352 therebetween. In accordance with an embodiment of the invention, a pulsatile flow of irrigation fluid can be directed within at least a portion of at least one of the inner core member 14, 114, 214, 314 and outer shell 16, 116, 216, 316 in Step 502. The irrigation fluid has a first flow rate in a first time period and has a second flow rate in a second time period. The first flow rate and the second flow rate can alternate and recur at intervals over time. The first flow rate and the second flow rate can alternate and recur at regular intervals in accordance with some embodiments of the disclosure and/or can alternate and recur at irregular intervals in accordance with other embodiments of the disclosure. The first flow rate and the second flow rate can be intermittent in an embodiment of the disclosure. In accordance with an embodiment of the disclosure, the second flow rate is greater than the first flow rate. For example and without limitation, the first flow rate can be approximately 2 ml/min, and the second flow rate can be approximately 13 ml/min. In accordance with other embodiments of the disclosure, the first flow rate can be greater than the second flow rate. Accordingly, the irrigation fluid is a pulsatile flow in alternating waves of low flow rates and high flow rates, where either a low flow rate occurs first or a high flow rate occurs first. Utilization of a first flow rate of irrigation fluid that is higher and a second flow rate of irrigation fluid that is lower can be preferred in some stepped irrigation sequences. Although these particular flow rates are mentioned in detail, the first and second flow rates can be smaller or greater in other embodiments of the disclosure.

The use of a pulsatile flow rate allows the temperature measurement from the thermal sensors 28 at the outer shell 16, 116, 216, 316 of the ablation electrode assembly 10, 110, 210, 310 as described herein to increase temporarily during the time period with a lower flow rate (i.e., the first time period), thereby bringing the temperature measurement from the thermal sensors 28 closer to the actual temperature of the interface between the ablation electrode assembly 10, 110, 210, 310 and the targeted tissue 13 so that the thermal sensors 28 more closely reflect the actual temperature. In particular, the method of using an ablation electrode assembly 10, 110, 210, 310 to control temperature during cardiac ablation of targeted tissue 13 can utilize an extended period of low flow (i.e., the first flow rate) early in the power delivery ablation cycle in order to provide a so-called "warm-up" sequence. The use of a pulsatile flow with an ablation electrode assembly 10, 110, 210, 310 having an inner core member 14, 114, 214, 314 and an outer shell 16, 116, 216, 316 can benefit most from the wave(s) of lower flow rates because the ablation electrode assembly 10, 110, 210, 310 already has an improved correlation between the temperatures of the ablation electrode assemblies 10, 110, 210, 310 and the targeted tissue. During the time period with a higher flow rate (i.e., the second time period), the ablation electrode assembly 10, 110, 210, 310 best receives the benefits of tissue cooling and coagulum reduction. Accordingly, the method of using an ablation electrode assembly 10, 110, 210, 310 to control temperature during cardiac ablation of targeted tissue can utilize higher flow rates (i.e., the second flow rate) to reduce the temperature of the interface between the electrode ablation assembly 10, 110, 210, 310 and the targeted tissue. In an exemplary embodiment of the disclosure, the method of using an ablation electrode assembly 10, 110, 210, 310 to control temperature during cardiac ablation of targeted tissue can employ the following pattern of flow rates: (1) an initial warm-up period; (2) a first flow rate (e.g., 2 ml/min) for a first time period (e.g., 6 seconds); (3) a first cool-down period; (4) a second flow rate (e.g., 13 ml/min) for a second time period (e.g., 4 seconds); (5) a recovery period; (6) a first flow rate (e.g., 2 ml/min) for a first time period (e.g., 6 seconds); (6) a second cool-down period; and (7) a second flow rate (e.g., 13 ml/min) for a second time period (e.g., 4 seconds). Pulsatile flow of irrigation fluid can also help prevent stagnation areas and increase flow turbulence, which can help prevent stasis and the formation of coagulum.

Valve members, for example and without limitation, such as those shown and described in co-owned U.S. Patent Application Publication No. 2008/0161795, or other similar flow control features can be used in connection with catheters incorporating ablation electrode assemblies 10, 110, 210, 310 in order to alternate between first and second flow rates. In other embodiments, the flow control features can be part of an ancillary control system separate from and to be used in conjunction with catheters. The valves can operate automatically without user input and/or can operate based on feedback recorded during RF ablation by the ECU 45. The feedback can relate to time, temperature, and/or impedance, for example and without limitation. For example, the first and second flow rates can be based at least in part on temperature measurements taken by the thermal sensors 28. For example, as temperature measurements from thermal sensors 28 increase, a higher flow rate can be desirable. For another example, as temperature measurements from thermal sensors 28 decrease, a lower flow rate can be desirable. The thermal sensors 28 can thus provide feedback which can be implemented in a control algorithm executed by the ECU 45 and/or control system 49 to automatically control the flow rates of irrigation fluid within catheters incorporating ablation electrode assembly 10, 110, 210, 310. For example, the first and second flow rates can be based at least in part on an impedance measurement taken by a positioning electrode as described hereinabove. In particular, the positioning electrodes can be used to sense an impedance at a particular location and transmit a representative signal to an external computer or processor (i.e., the ECU 45). Circuitry for implementing the feedback automatically in a control algorithm can be readily provided by those having ordinary skill in the art after becoming familiar with the teachings herein. Although pulsatile flow of irrigation fluid is mentioned and described in detail, other flow patterns for irrigation fluid (e.g., intermittent, constant, variable) can be used in connection with other embodiments of the invention.

Although at least four embodiments of this disclosure and at least two methods of use therefor have been described above with a certain degree of particularity, those skilled in the art could make numerous alterations to the disclosed embodiments without departing from the spirit or scope of this disclosure. For example, additional thermal sensors can be connected to the ablation electrode assemblies (e.g., external to the outer shell) for additional temperature measurements. For another example, although the ablation electrode assemblies include an irrigation port as described and illustrated and although exemplary methods of using ablation electrode assemblies to provide irrigation fluid have been described and illustrated, the ablation electrode assemblies could be used and provide benefits even if irrigation fluid is not utilized in the ablation electrode assemblies. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure can be made without departing from the spirit of the disclosure as defined in the appended claims.

What is claimed is:
1. An ablation electrode assembly comprising:
  an inner core member having a distal end, a proximal end, and a longitudinal axis, wherein the inner core member comprises a thermal insulator having a reduced thermal conductivity; and an outer shell surrounding at least a portion of the inner core member, the outer shell having a distal end and a proximal end, wherein the outer shell comprises an electrically conductive material;

wherein the inner core member includes a plurality of channels located on an outer surface of the inner core member;

wherein each of the plurality of channels includes a thermal sensor disposed therein; and wherein the inner core member and the outer shell define a non-irrigated space therebetween configured to interrupt or reduce a heat transfer path between the thermal sensors.

2. The ablation electrode assembly of claim 1, wherein the inner core member and the outer shell define a space therebetween configured to interrupt or reduce a heat transfer path between the thermal sensors disposed in each of the plurality of channels.

3. The ablation electrode assembly of claim 2, wherein the space is annular.

4. The ablation electrode assembly of claim 2, where the space comprises a vacuum or evacuated region.

5. The ablation electrode assembly of claim 1, wherein the inner core member comprises:
an inner surface defining an inner cavity, and
a radially extending passageway, relative to the longitudinal axis of the inner core member, that extends from the inner cavity to the outer surface of the inner core member.

6. The ablation electrode assembly of claim 1, wherein the inner core member further comprises an axially extending passageway, relative to the longitudinal axis of the inner core member, extending from an inner cavity of the inner core member to the distal end of the inner core member.

7. The ablation electrode assembly of claim 1, wherein the outer shell is scored with a plurality of axially extending slots, relative to the longitudinal axis of the inner core member, to separate the outer shell into a plurality of segments.

* * * * *